United States Patent
Crews et al.

(10) Patent No.: US 8,961,539 B2
(45) Date of Patent: Feb. 24, 2015

(54) ENDOSCOPIC IMPLANT SYSTEM AND METHOD

(75) Inventors: Samuel T. Crews, Woodside, CA (US); Brett Swope, Gaithersburg, MD (US); Justen England, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1102 days.

(21) Appl. No.: 12/435,344

(22) Filed: May 4, 2009

(65) Prior Publication Data

US 2010/0280529 A1  Nov. 4, 2010

(51) Int. Cl.
- A61B 17/10 (2006.01)
- A61B 17/29 (2006.01)
- A61F 5/00 (2006.01)
- A61B 17/00 (2006.01)
- A61B 17/064 (2006.01)

(52) U.S. Cl.
CPC ............... *A61B 17/29* (2013.01); *A61F 5/0086* (2013.01); *A61B 2017/003* (2013.01); *A61B 2017/00827* (2013.01); *A61B 2017/0641* (2013.01); *A61F 5/0089* (2013.01)
USPC ......................................................... 606/139

(58) Field of Classification Search
CPC ............. A61B 17/29; A61B 2017/003; A61B 2017/00827; A61B 2017/0641; A61F 5/0086; A61F 5/0089
USPC .................................. 606/139, 153, 157, 167
See application file for complete search history.

(56) References Cited

U.S. PATENT DOCUMENTS

| | | | |
|---|---|---|---|
| 1,408,865 A | 3/1922 | Cowell | |
| 3,663,965 A | 5/1972 | Lee et al. | |
| 4,134,405 A | 1/1979 | Smit | |
| 4,207,890 A | 6/1980 | Mamajek et al. | |

(Continued)

FOREIGN PATENT DOCUMENTS

| | | | |
|---|---|---|---|
| CH | 680263 A5 | 7/1992 | |
| EP | 0 775 471 A1 | 5/1997 | |

(Continued)

OTHER PUBLICATIONS

International Search Report from PCT Patent Application No. PCT/US2002/027177 mailed Feb. 14, 2003.

(Continued)

*Primary Examiner* — Thomas McEvoy
*Assistant Examiner* — Julie A Szpira
(74) *Attorney, Agent, or Firm* — Bookoff McAndrews, PLLC

(57) ABSTRACT

A system, device, device and method for implanting a food restrictor in a patient's stomach, by coupling the restrictor to a plurality of tissue-plication anchors already placed in the stomach, are disclosed. The device includes an elongate shaft assembly for accessing the stomach transorally, and on which the restrictor can be carried, and a plurality of cable members mounted on the shaft assembly. The cable members are disposed on the shaft assembly along a distal section thereof, and releasably attached to the shaft assembly's distal end. After a cable member engages a tissue-plication anchor, retracting the cable is operable to first release the member from a holder at the distal end of the shaft assembly, then pull a portion of the anchor through an aperture in the restrictor. This process is repeated for each anchor in the stomach for attaching the restrictor to the stomach.

20 Claims, 15 Drawing Sheets

(56) References Cited

U.S. PATENT DOCUMENTS

| | | |
|---|---|---|
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,501,264 A | 2/1985 | Rockey |
| 4,607,618 A | 8/1986 | Angelchik |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galtier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. |
| 5,061,275 A | 10/1991 | Wallsten et al. |
| 5,084,061 A | 1/1992 | Gau et al. |
| 5,088,979 A | 2/1992 | Filipi et al. |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shlain |
| 5,401,241 A | 3/1995 | Delany |
| 5,403,326 A | 4/1995 | Harrison et al. |
| 5,405,377 A | 4/1995 | Cragg |
| 5,431,673 A | 7/1995 | Summers et al. |
| 5,486,187 A | 1/1996 | Schenck |
| 5,514,176 A | 5/1996 | Bosley, Jr. |
| 5,535,935 A | 7/1996 | Vidal et al. |
| 5,562,239 A | 10/1996 | Boiarski et al. |
| 5,571,116 A | 11/1996 | Bolanos et al. |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas et al. |
| 5,630,539 A | 5/1997 | Plyley et al. |
| 5,647,526 A | 7/1997 | Green et al. |
| 5,653,743 A | 8/1997 | Martin |
| 5,662,713 A | 9/1997 | Andersen et al. |
| 5,673,841 A | 10/1997 | Schulze et al. |
| 5,674,241 A | 10/1997 | Bley et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendijk et al. |
| 5,762,255 A | 6/1998 | Chrisman et al. |
| 5,771,903 A | 6/1998 | Jakobsson |
| 5,785,684 A | 7/1998 | Zimmon |
| 5,820,584 A | 10/1998 | Crabb |
| 5,839,639 A | 11/1998 | Sauer et al. |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,868,141 A | 2/1999 | Ellias |
| 5,887,594 A | 3/1999 | LoCicero, III |
| 5,897,562 A | 4/1999 | Bolanos et al. |
| 5,910,144 A | 6/1999 | Hayashi |
| 5,922,019 A | 7/1999 | Hankh et al. |
| 5,947,983 A | 9/1999 | Solar et al. |
| 5,993,473 A | 11/1999 | Chan et al. |
| 5,993,483 A | 11/1999 | Gianotti |
| 6,016,848 A | 1/2000 | Egres, Jr. |
| 6,051,015 A | 4/2000 | Maahs |
| 6,086,600 A | 7/2000 | Kortenback |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,146,416 A | 11/2000 | Andersen et al. |
| 6,159,146 A | 12/2000 | El Gazayerli |
| 6,159,238 A | 12/2000 | Killion et al. |
| 6,179,195 B1 * | 1/2001 | Adams et al. ............... 227/180.1 |
| 6,197,022 B1 | 3/2001 | Baker |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,312,437 B1 * | 11/2001 | Kortenbach ................... 606/139 |
| 6,358,197 B1 | 3/2002 | Silverman |
| 6,416,522 B1 | 7/2002 | Strecker |
| 6,425,916 B1 | 7/2002 | Garrison et al. |
| 6,454,785 B2 | 9/2002 | De Hoyos Garza |
| 6,460,543 B1 | 10/2002 | Forsell |
| 6,461,366 B1 | 10/2002 | Seguin |
| 6,494,888 B1 | 12/2002 | Laufer et al. |
| 6,494,895 B2 | 12/2002 | Addis |
| 6,503,264 B1 | 1/2003 | Birk |
| 6,506,196 B1 | 1/2003 | Laufer et al. |
| 6,527,784 B2 | 3/2003 | Adams et al. |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor et al. |
| 6,572,627 B2 | 6/2003 | Gabbay |
| 6,572,629 B2 | 6/2003 | Kalloo |
| 6,575,896 B2 | 6/2003 | Silverman |
| 6,592,596 B1 | 7/2003 | Geitz |
| 6,596,023 B1 | 7/2003 | Nunez et al. |
| 6,607,555 B2 | 8/2003 | Patterson et al. |
| 6,613,060 B2 * | 9/2003 | Adams et al. ................... 606/157 |
| 6,627,206 B2 | 9/2003 | Lloyd |
| 6,632,227 B2 | 10/2003 | Adams |
| 6,663,639 B1 | 12/2003 | Laufer et al. |
| 6,675,809 B2 | 1/2004 | Stack et al. |
| 6,740,098 B2 | 5/2004 | Abrams et al. |
| 6,740,121 B2 | 5/2004 | Geitz |
| 6,746,460 B2 | 6/2004 | Gannoe et al. |
| 6,755,869 B2 | 6/2004 | Geitz |
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,821,285 B2 | 11/2004 | Laufer et al. |
| 6,835,200 B2 | 12/2004 | Laufer et al. |
| 6,845,776 B2 | 1/2005 | Stack et al. |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapacki et al. |
| 7,020,531 B1 | 3/2006 | Colliou et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,056,305 B2 | 6/2006 | Garza Alvarez |
| 7,066,945 B2 | 6/2006 | Hashiba et al. |

(56) References Cited

U.S. PATENT DOCUMENTS

| | | |
|---|---|---|
| 7,083,629 B2 | 8/2006 | Weller et al. |
| 7,090,699 B2 | 8/2006 | Geitz |
| 7,097,650 B2 | 8/2006 | Weller et al. |
| 7,097,665 B2 | 8/2006 | Stack et al. |
| 7,111,627 B2 | 9/2006 | Stack et al. |
| 7,112,186 B2 | 9/2006 | Shah |
| 7,120,498 B2 | 10/2006 | Imran et al. |
| 7,121,283 B2 | 10/2006 | Stack et al. |
| 7,146,984 B2 | 12/2006 | Stack et al. |
| 7,147,140 B2 | 12/2006 | Wukusick et al. |
| 7,152,607 B2 | 12/2006 | Stack et al. |
| 7,153,314 B2 * | 12/2006 | Laufer et al. ............ 606/153 |
| 7,160,312 B2 | 1/2007 | Saadat |
| 7,172,613 B2 | 2/2007 | Wazne |
| 7,175,638 B2 | 2/2007 | Gannoe et al. |
| 7,175,660 B2 | 2/2007 | Cartledge et al. |
| 7,211,114 B2 | 5/2007 | Bessler et |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,255,675 B2 | 8/2007 | Gertner et al. |
| 7,261,722 B2 | 8/2007 | McGuckin, Jr. et al. |
| 7,288,101 B2 | 10/2007 | Deem et al. |
| 7,306,614 B2 | 12/2007 | Weller et al. |
| 7,315,509 B2 | 1/2008 | Jeong et al. |
| 7,316,716 B2 | 1/2008 | Egan |
| 7,320,696 B2 | 1/2008 | Gazi et al. |
| 7,326,207 B2 | 2/2008 | Edwards |
| 7,335,210 B2 | 2/2008 | Smit |
| 7,347,863 B2 | 3/2008 | Rothe et al. |
| 7,347,875 B2 | 3/2008 | Levine et al. |
| 7,354,454 B2 | 4/2008 | Stack et al. |
| 7,399,304 B2 | 7/2008 | Gambale et al. |
| 7,431,725 B2 | 10/2008 | Stack et al. |
| 7,461,767 B2 | 12/2008 | Viola et al. |
| 7,470,251 B2 | 12/2008 | Shah |
| 7,485,142 B2 | 2/2009 | Milo |
| 7,503,922 B2 | 3/2009 | Deem et al. |
| 7,520,884 B2 | 4/2009 | Swanstrom et al. |
| 7,713,277 B2 * | 5/2010 | Laufer et al. ............ 606/153 |
| 7,736,373 B2 * | 6/2010 | Laufer et al. ............ 606/153 |
| 7,896,215 B2 * | 3/2011 | Adams et al. ............ 227/180.1 |
| 7,998,148 B2 * | 8/2011 | Pasricha et al. ........... 606/139 |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0044595 A1 | 11/2001 | Reydel et al. |
| 2002/0022851 A1 | 2/2002 | Kalloo et al. |
| 2002/0055757 A1 | 5/2002 | Torre et al. |
| 2002/0072761 A1 | 6/2002 | Abrams et al. |
| 2002/0082621 A1 | 6/2002 | Schurr et al. |
| 2002/0099439 A1 | 7/2002 | Schwartz et al. |
| 2002/0183768 A1 | 12/2002 | Deem et al. |
| 2003/0009236 A1 | 1/2003 | Godin |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0120289 A1 | 6/2003 | McGuckin, Jr. et al. |
| 2003/0191476 A1 | 10/2003 | Smit |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2003/0220660 A1 | 11/2003 | Kortenbach et al. |
| 2003/0233140 A1 * | 12/2003 | Hartley et al. ............ 623/1.11 |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0044364 A1 | 3/2004 | DeVries et al. |
| 2004/0068276 A1 * | 4/2004 | Golden et al. ............ 606/153 |
| 2004/0082963 A1 | 4/2004 | Gannoe et al. |
| 2004/0088023 A1 | 5/2004 | Imran et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0098043 A1 | 5/2004 | Trout |
| 2004/0107004 A1 | 6/2004 | Levine et al. |
| 2004/0117031 A1 | 6/2004 | Stack et al. |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162568 A1 | 8/2004 | Saadat et al. |
| 2004/0172141 A1 | 9/2004 | Stack et al. |
| 2004/0210243 A1 | 10/2004 | Gannoe et al. |
| 2004/0215216 A1 | 10/2004 | Gannoe et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0243223 A1 | 12/2004 | Kraemer et al. |
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0049718 A1 | 3/2005 | Dann et al. |
| 2005/0075654 A1 | 4/2005 | Kelleher |
| 2005/0080444 A1 | 4/2005 | Kraemer et al. |
| 2005/0085787 A1 | 4/2005 | Laufer |
| 2005/0096673 A1 | 5/2005 | Stack et al. |
| 2005/0096750 A1 | 5/2005 | Kagan et al. |
| 2005/0159769 A1 | 7/2005 | Alverdy |
| 2005/0177181 A1 | 8/2005 | Kagan et al. |
| 2005/0192599 A1 | 9/2005 | Demarais |
| 2005/0192615 A1 | 9/2005 | Torre et al. |
| 2005/0216042 A1 | 9/2005 | Gertner |
| 2005/0247320 A1 | 11/2005 | Stack et al. |
| 2005/0251158 A1 | 11/2005 | Saadat et al. |
| 2005/0251162 A1 | 11/2005 | Rothe et al. |
| 2005/0256533 A1 | 11/2005 | Roth et al. |
| 2005/0261712 A1 | 11/2005 | Balbierz et al. |
| 2005/0267499 A1 | 12/2005 | Stack et al. |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0015006 A1 * | 1/2006 | Laurence et al. ............ 600/104 |
| 2006/0020278 A1 | 1/2006 | Burnette et al. |
| 2006/0058829 A1 | 3/2006 | Sampson et al. |
| 2006/0120289 A1 | 6/2006 | Cunningham, Jr. |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0178560 A1 | 8/2006 | Saadat et al. |
| 2006/0178691 A1 | 8/2006 | Binmoeller |
| 2006/0195139 A1 | 8/2006 | Gertner |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0239284 A1 | 10/2007 | Skerven et al. |
| 2007/0244493 A1 * | 10/2007 | Bjerken ............ 606/139 |
| 2007/0260327 A1 | 11/2007 | Case et al. |
| 2007/0276432 A1 | 11/2007 | Stack et al. |
| 2008/0033574 A1 | 2/2008 | Bessler et al. |
| 2008/0065122 A1 | 3/2008 | Stack et al. |

(56) References Cited

U.S. PATENT DOCUMENTS

| | | |
|---|---|---|
| 2008/0116244 A1 | 5/2008 | Rethy et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0269797 A1 | 10/2008 | Stack et al. |
| 2008/0294179 A1 | 11/2008 | Balbierz et al. |
| 2009/0018558 A1 | 1/2009 | Laufer et al. |
| 2009/0024143 A1* | 1/2009 | Crews et al. ............ 606/139 |
| 2009/0030284 A1 | 1/2009 | Cole et al. |
| 2009/0125040 A1 | 5/2009 | Hambly et al. |
| 2011/0270275 A1* | 11/2011 | Cassivi ................. 606/139 |

FOREIGN PATENT DOCUMENTS

| | | |
|---|---|---|
| EP | 1492478 | 1/2005 |
| EP | 1 602 336 A2 | 12/2005 |
| FR | 2768324 A1 | 3/1999 |
| JP | 09-168597 | 6/1997 |
| WO | WO 91/01117 A1 | 2/1991 |
| WO | WO 97/47231 A2 | 12/1997 |
| WO | WO 00/12027 A1 | 3/2000 |
| WO | WO 00/32137 A1 | 6/2000 |
| WO | WO 00/78227 A1 | 12/2000 |
| WO | WO 01/41671 | 6/2001 |
| WO | WO 01/45485 A2 | 6/2001 |
| WO | WO 01/49359 A1 | 7/2001 |
| WO | WO 01/66018 A1 | 9/2001 |
| WO | WO 01/85034 A1 | 11/2001 |
| WO | WO 01/89393 A1 | 11/2001 |
| WO | WO 02/060328 A1 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 A2 | 11/2003 |
| WO | WO 03/094785 | 11/2003 |
| WO | WO 03/099137 A2 | 12/2003 |
| WO | WO 2004/019765 | 3/2004 |
| WO | WO 2004/019787 | 3/2004 |
| WO | WO 2004/032760 A2 | 4/2004 |
| WO | WO 2004/037064 | 5/2004 |
| WO | WO 2004/041133 | 5/2004 |
| WO | WO 2004/064680 | 8/2004 |
| WO | WO 2004/064685 | 8/2004 |
| WO | WO 2004/080336 | 9/2004 |
| WO | WO 2004/110285 A1 | 12/2004 |
| WO | WO 2005/037152 A1 | 4/2005 |
| WO | WO 2005/079673 A2 | 9/2005 |
| WO | WO 2005/096991 A1 | 10/2005 |
| WO | WO 2005/105003 | 11/2005 |
| WO | WO 2006/016894 A1 | 2/2006 |
| WO | WO 2006/055365 A2 | 5/2006 |
| WO | WO 2006/127593 | 11/2006 |
| WO | WO 2007/041598 A1 | 4/2007 |
| WO | WO 2008/030403 | 3/2008 |
| WO | WO 2008/033409 | 3/2008 |
| WO | WO 2008/033474 | 3/2008 |
| WO | WO 2009/011881 | 1/2009 |
| WO | WO 2009/086549 | 7/2009 |
| WO | WO 2009/117533 | 9/2009 |
| WO | WO 2010/054399 | 5/2010 |
| WO | WO 2010/054404 | 5/2010 |

OTHER PUBLICATIONS

International Search Report from PCT Patent Application No. PCT/US2003/004378 mailed Aug. 13, 2003.
International Search Report from PCT Patent Application No. PCT/US2003/033605 mailed Mar. 29, 2004.
International Search Report from PCT Patent Application No. PCT/US2003/033606 mailed Mar. 29, 2004.
International Search Report from PCT Patent Application No. PCT/US2003/004449 mailed Aug. 13, 2003.
International Search Report from PCT Patent Application No. PCT/US2004/006695 mailed Sep. 8, 2004.
International Search Report from PCT Patent Application No. PCT/US2004/033007 mailed Feb. 9, 2005.
International Search Report from PCT Patent Application No. PCT/US2005/014372 mailed Jul. 28, 2005.
International Search Report from PCT Patent Application No. PCT/US2006/019727 mailed Apr. 19, 2007.
International Search Report from PCT Patent Application No. PCT/US2006/038684 mailed Feb. 14, 2007.
International Search Report from PCT Patent Application No. PCT/US2007/019227 mailed Feb. 20, 2008.
International Search Report from PCT Patent Application No. PCT/US2007/019833 mailed Feb. 20, 2008.
International Search Report from PCT Patent Application No. PCT/US2007/019940 mailed Mar. 14, 2008.
International Search Report from PCT Patent Application No. PCT/US2008/008726 mailed Oct. 16, 2008.
International Search Report from PCT Patent Application No. PCT/US2008/008729 mailed Aug. 18, 2009.
International Search Report from PCT Patent Application No. PCT/US2008/063440 mailed Aug. 1, 2008.
International Search Report from PCT Patent Application No. PCT/US2008/088581 mailed Feb. 26, 2009.
International Search Report from PCT Patent Application No. PCT/US2009/037586 mailed Sep. 28, 2009.
International Search Report from PCT Patent Application No. PCT/US2009/063925 mailed Jan. 12, 2010.
International Search Report from PCT Patent Application No. PCT/US2009/063930 mailed Jan. 12, 2010.
Felsher, et al., "Mucosal apposition in endoscopic suturing", Gastrointestinal Endoscopy, vol. 58, No. 6, pp. 867-870, (2003).
Cole et al., Utility U.S. Appl. No. 12/050,169, filed Mar. 18, 2008, U.S. Appl. No. 12/050,169, 85 pages (2008).
Stecco, K. et al., "Trans-Oral Plication Formation and Gastric Implant Placement in a Canine Model", Stecco Group, San Jose and Barosnese, Inc., Redwood City, California (2004).
Stecco, K. et al., "Safety of a Gastric Restrictive Implant in a Canine Model", Stecco Group, San Jose and Barosnese, Inc., Redwood City, California (2004).
U.S. Appl. No. 12/050,169, Cole et al.

* cited by examiner

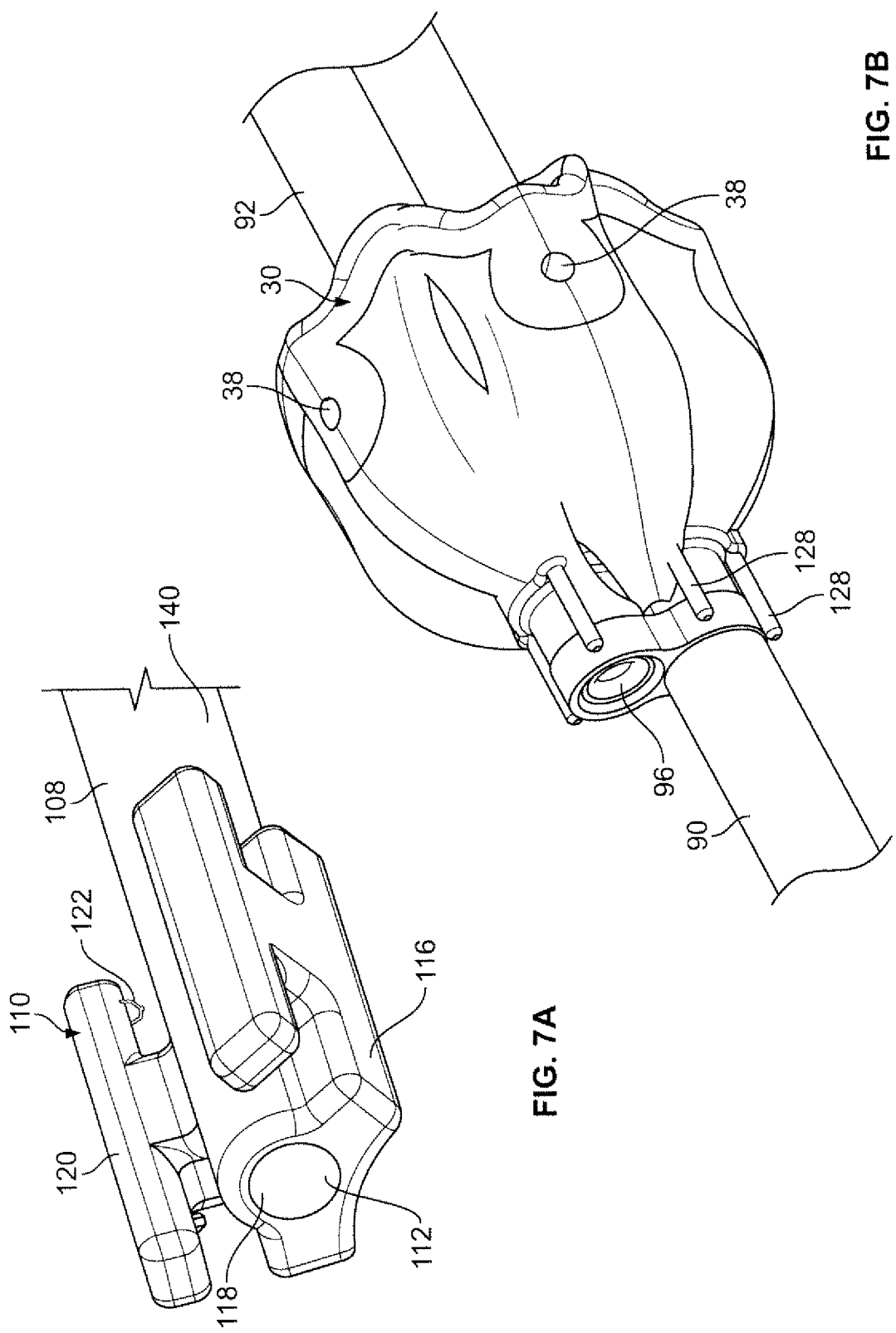

ENDOSCOPIC IMPLANT SYSTEM AND METHOD

FIELD OF THE INVENTION

The present invention relates to a device and method for accessing multiple targets within a hollow organ, for example, for use in attaching an implant to tissue-supported anchors within the organ.

BACKGROUND OF THE INVENTION

Non-invasive surgery to attach a medical implant within the body, e.g., within the interior of a hollow organ such as the stomach, has become an important surgical option. For example, bariatric surgery to limit food intake into the stomach, in the treatment of obesity, can now be done transorally, rather than having to penetrate the peritoneal cavity. In a transoral procedure, an access tube is placed in the patient's esophagus, as a guide for one more or more endoscopic tools used in attaching an implant to, and/or reconfiguring, the stomach.

An anatomical view of a human stomach S and associated features is shown in FIG. 1. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

Several prior applications, including U.S. Publication No. US 2007/0276432; having a priority date of Oct. 8, 2004 and U.S. Publication No. US 2008/0065122, filed May 23, 2006 describe methods according to which medical implants are coupled to tissue structures, such as plications or folds, formed within the stomach. Examples of methods and devices for forming such tissue structures are described in U.S. Publication No. US 2007/0219571 (entitled ENDOSCOPIC PLICATION DEVICES AND METHOD), filed Oct. 3, 2006, U.S. application Ser. No. 11/900,757 (entitled ENDOSCOPIC PLICATION DEVICE AND METHOD), filed Sep. 13, 2007, and U.S. application Ser. No. 12/050,169 (entitled ENDOSCOPIC STAPLING DEVICES AND METHODS), filed Mar. 18, 2008. Each of the referenced publications and applications is incorporated herein by reference.

As disclosed in these prior applications, more robust and long lasting coupling between the implant and the surrounding stomach wall tissue is achieved when the plications/folds are formed by retaining regions of serosal tissue (i.e., the tissue on the exterior surface of the stomach) in contact with one another. Over time, adhesions form between the opposed serosal layers. These adhesions help to create strong bonds that can facilitate retention of the plication fold over extended durations, despite the forces imparted on them by stomach movement and implanted devices Several of the disclosed methods for forming tissue plications include a step in which a hole or cut is formed in the plication, using the plication forming device or a separate tissue-cutting device. Typically, the device also fastens the fold with an array of staples that are formed in the tissue about the hole. An example of this type of stapled tissue plication is shown in FIG. 2A, which is a cross-section taken along line 2B-2B in FIG. 1. Stapling devices and methods for forming such stapled tissue folds of this type are described in co-owned U.S. application Ser. No. 11/542,457, entitled ENDOSCOPIC PLICATION DEVICES AND METHODS, filed Oct. 3, 2006, and published Sep. 20, 2007 as US 2007-0219571, and co-owned U.S. application Ser. No. 12/050,169, entitled ENDOSCOPIC STAPLING DEVICES AND METHODS, filed Mar. 18, 2008, both and incorporated herein by reference.

In a typical procedure that uses the stapled plications for implant attachment, a plurality of stapled tissue plications, each with an anchor-receiving hole, are formed in a tissue, such as illustrated in FIGS. 2A and 2B. In the latter figure, five such plications are formed in the interior of the stomach, for attaching a food-restrictive pouch, or restrictor, near a patient's esophagus, to limiting food intake by the patient. After formation of the plications, an anchor (FIG. 2C) is placed in each hole (FIG. 2D), and the implant, e.g., restrictor, is attached to the plications by introducing, for each plication, an anchor that extends through the hole and through an anchor-receiving aperture in the implant (FIG. 2E). By way of illustration, for placement of a stomach restrictor attached to five plications formed within the stomach (FIG. 2F), the implant operation will require ten separate steps in which an endoscopic device is placed in and then removed from the stomach transorally: five for forming each of the stomach plications, and five for each anchor placement between a plication and anchor-receiving aperture in the restrictor. A system and method for implanting a food-restrictive device of this type are detailed in co-owned U.S. application Ser. No. 12/175,242, filed Jul. 17, 2008, corresponding to PCT application PCT/US2008/008729, which is incorporated herein in its entirety.

Given the surgical time and inconvenience, and the patient discomfort, associated with each transoral-accessing step, it would be desirable to reduce the number of accessing steps needed for attaching an implant to a tissue plication. Co-owned U.S. patent application Ser. No. 12/434,226 for PLICATION TAGGING DEVICE AND METHOD, filed May 1, 2009, discloses a device and method for placing an anchor in the plication at the time the plication is formed, thus reducing to five the number of accessing steps needed to place five tissue-attached anchors within the stomach. The present application discloses a device and method capable of accessing a plurality of spaced targets within the organ, such as the five tissue-supported anchors, and optionally, for attaching an implant to the targets in a single accessing step.

SUMMARY OF THE INVENTION

The invention includes, in one aspect, a device for engaging a plurality of tissue targets within a hollow organ of a subject. The device includes an elongate shaft assembly having a proximal section terminating at a proximal end and a distal section terminating at a distal end. The shaft assembly comprises (a) a cable holder carried at the distal end of the shaft assembly, (b) a plurality of cable members extending along the shaft assembly, each cable member including (i) a cable whose axial position can be manipulated from the proximal end of the assembly and (ii) a distal-end tool for engaging a selected tissue target within the hollow organ, (c) for each cable member, a release structure for releasably attaching the associated cable on the holder, and (d) a steering mechanism extending along the shaft assembly by which the cable holder can be manipulated from the proximal end of the assembly to place a selected cable member tool adjacent a selected target within the organ.

With a selected cable-assembly tool positioned adjacent a selected tissue target and the tool manipulated to engage the selected target, axial movement of the tissue-engaged cable with respect to the holder and/or release of the cable from the holder allows the holder and its remaining attached cable members to be moved to place the tool of another selected cable member in position for engaging another selected tissue target.

The distal section of the shaft assembly may be detachable from the assembly's proximal section, for replacement or cleaning The device may further include an endoscope carried on the shaft assembly, independently movable with respect to the cable holder at the distal end of the shaft assembly.

A proximal portion of each cable member may be disposed within a shaft assembly casing extending along the proximal section of the shaft assembly, and an exposed distal portion may be disposed along the distal section thereof, which is substantially less than proximal portion. The portion of each cable member disposed within the shaft assembly casing may be housed within a cable sheath.

The holder may include, for each cable member, an axially extending slot formed in the holder, and the release structure may include a passive capture member adapted to releasably hold the cable assembly within the slot, for axial movement therein, but deform when the tool and an engaged tissue target are pulled away from the slot, to release the cable member and engaged tool from the holder. Alternatively, the release structure in each holder may include an active capture member whose operation can be controlled at the proximal end of the shaft assembly between a capture position, in which the cable assembly is supported within the holder slot, for axial movement therein, and a release position in which the cable member and engaged tissue target are released from the holder.

In another general embodiment, the exposed portion of each cable member is housed within an axially compressible sheath that allows that distal end of the cable to be retracted, shortening the length of the exposed portion of the exposed portion of the cable member. The distal sheath of each cable member may have axially extending slots, to enhance the axial compressibility of the sheath. The release structure in this embodiment may be a distal-end fixture at the distal end of the sheath and which is releasably attached by friction fit to the holder. The distal-end fixture may be dimensioned to block the cable tool and attached tissue target, such that retracting the cable and engaged target against the distal-end fixture is effective, with further retraction, to pull the fixture, cable member and engaged tissue from the holder.

The cable in each cable member may include an inner wire that is axially shiftable within the cable, and the cable-assembly tool may include a pair of clamp arms carried at the distal end of the wire, such that movement of the wire within the cable in distal and proximal directions is effective to open and close the clamp arms, respectively.

The device may be used, for example, in attaching a restrictor within a subject's stomach to a plurality of tissue targets having anchors fastened to tissue plications within the stomach, where the restrictor includes a proximal opening and a plurality of apertures spaced about the proximal opening, each for engaging an anchor to attach the restrictor within the stomach. In this embodiment, the shaft assembly may include a restrictor mount for holding the restrictor releasably on the shaft assembly, with the cable members received through the restrictor apertures, and the cable-assembly tools may be adapted to clamp the anchors, such that withdrawing a cable in a selected cable member, after clamping a selected anchor, is effective to release the cable member from its release structure in the distal-end holder, allowing the tool and engaged anchor to be retracted distally until a cap portion of the anchor is pulled through the associated aperture in the restrictor. The restrictor may have a central distal opening, and may be adapted to be carried on the device with a distal portion of the shaft assembly inserted through the distal opening in the restrictor, where the restrictor is forced into collapsed condition when the cable members are attached to the distal-end holder. The restrictor mount may have a plurality of posts positioned about the shaft assembly, for mounting the restrictor on the shaft assembly, with the posts received in apertures spaced about the restrictor's distal opening, wherein the restrictor can be disengaged from the device only when all of the cable members have been released from the holder.

Also disclosed is a system for implanting in a patient's stomach, adjacent the gastro-esophageal junction thereof, a restrictor of the type having a proximal opening for receiving food from the patient's esophagus, and a plurality of apertures spaced about the opening, each for engaging an tissue-supported anchor, to attach the restrictor within the stomach. The system includes (A) an implantation device comprising an elongate shaft assembly having a proximal section terminating at a proximal end and a distal section terminating at a distal end, where the shaft assembly comprises (a) a cable holder carried at the distal end of the assembly, (b) a plurality of cable members extending along the shaft assembly, each cable member including a cable whose axial position can be manipulated from the proximal end of the assembly, and a distal-end tool for engaging a selected tissue supported-anchor within the stomach, (c) for each cable member, a release structure for releasable attaching the associated cable on the holder, (d) a steering mechanism by which the cable holder can be manipulated from the proximal end of the assembly, to place a selected cable member tool adjacent a selected tissue-supported anchor the organ, and (e) a restrictor mount carried on the shaft assembly's distal end section, for supporting the restrictor thereon.

With a selected cable-member tool positioned adjacent a selected tissue-supported anchor and its tool manipulated to engage that anchor, axial movement of the anchor-engaged cable with respect to the holder and/or release of the cable from the holder allows the holder and its remaining supported cable members to be moved to place the tool of another selected cable member in position for engaging another selected tissue-supported anchor, and retracting the tool and engaged anchor is operable to successively (i) release the assembly tool and attached anchor from the release structure in the holder, and (ii) pull a cap of the anchor through the restrictor aperture, to attach that anchor to the restrictor Also forming part of the system is an overtube adapted for transoral placement in a patient, by which the device can be placed in the patient's stomach. The overtube may be axially movable on the device's shaft assembly between extended and retracted positions at which the overtube covers and exposes the restrictor mount and restrictor carried thereon, respectively.

The restrictor mount in the system device may have a plurality of posts positioned about the shaft assembly, with the posts received in apertures spaced about the restrictor's distal opening, and wherein the restrictor can be disengaged from the device only when all of the cable members have been released from the holder.

In another aspect, the invention includes a method for implanting in a patient's stomach, adjacent the gastro-esophageal junction thereof, a restrictor of the type having a proximal opening for receiving food from the patient's esophagus, and a plurality of apertures spaced about the opening, each for engaging an tissue-supported anchor to attach the restrictor within the stomach. The method comprises the steps of:

(a) forming within the patient's stomach, adjacent the gastro-esophageal junction, a plurality of tissue plications, each supporting an anchor that is in contact with opposite sides of the plication, and which provides an elastomeric cap for anchoring to the restrictor;

(b) accessing the patient's stomach with an endoscopic device having a shaft assembly with a distal end holder that can be moved within the patient's stomach to selected positions, and a plurality of cable members releasably attached to holder, for movement therewith, each assembly having a distal-end tool operable to engage an anchor cap, where the restrictor is carried on the distal section of the device with the plurality of cable members received through the plurality of restrictor apertures;

(c) manipulating the device to position the holder adjacent a selected plication anchor in the stomach;

(d) manipulating the tool of a selected cable member to engage the cap of the anchor at the selected plication, (e) without having to remove the device from the patient's stomach, repeating steps (c) and (d) until each cable member has been attached to each anchor; and (f) before or after repeating steps (c) and (d) for any selected anchor, pulling the selected cable member tool and engaged anchor cap in a proximal direction through the associated aperture in the restrictor; and (g) before or after each step (f), releasing the engaged anchor caps from the associated cable-assembly tool, and withdrawing the device from the patient's stomach.

The cable members may be releasably attached to the device's distal-end holder, wherein step (f) may include retracting the cable member tool and engaged anchor cap to release the tool from the distal-end holder.

These and other objects and features of the invention will become more fully apparent when the following detailed description of the invention is read in conjunction with the accompanying drawings.

BRIEF DESCRIPTION OF THE DRAWINGS

FIG. 7A is an enlarged perspective view of a distal-end fixture in a cable assembly in the device illustrated in FIGS. 6A and 6B.

FIGS. 7B and 7C are enlarged perspective views of the distal end of the device in FIGS. 6A and 6B, before (FIG. 7A) and after (FIG. 7B) placement of a restrictor on the device.

DETAILED DESCRIPTION OF THE DRAWINGS

The system and device of the present invention are designed for engaging a plurality of spaced tissue targets within a hollow organ of a subject, such as the stomach. The targets that are accessed may be organ tissue itself, when it is desired to manipulate two or more organ tissue regions, for example, when reconfiguring the stomach in a bariatric operation to reduce stomach volume. More typically, the tissue targets to be engaged are fasteners, sutures, anchors, or the like that have been attached at selected regions within the organ, where "engaging a tissue target" means engaging a fastener, suture, anchor or the like that is attached to a tissue at a target region.

Tissue Plications for Coupling a Restrictor Implant to the Stomach

Figure 1:
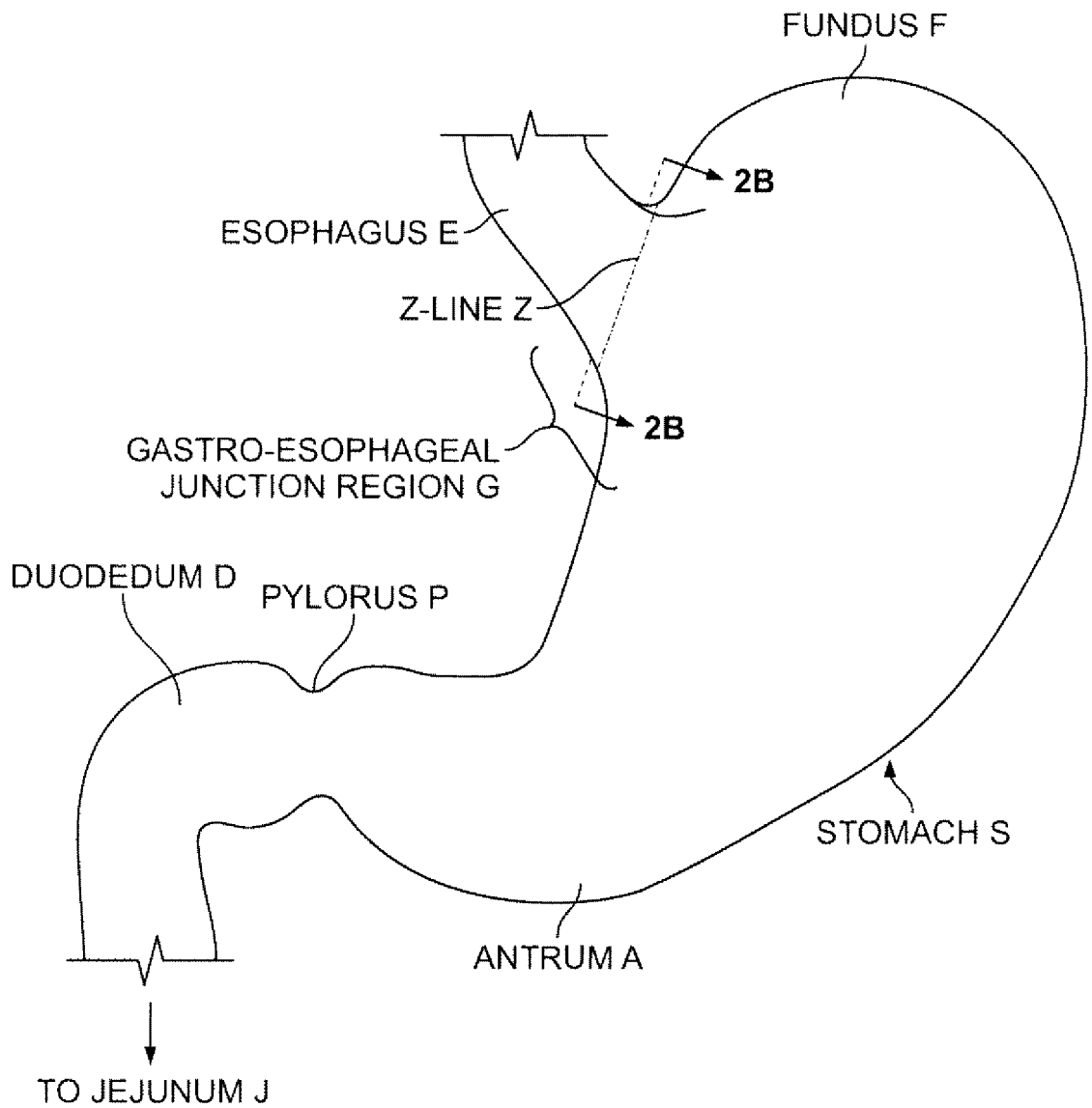
FIG. 1 is a schematic illustration of a human stomach and a portion of the small intestine.
Figure 2A:
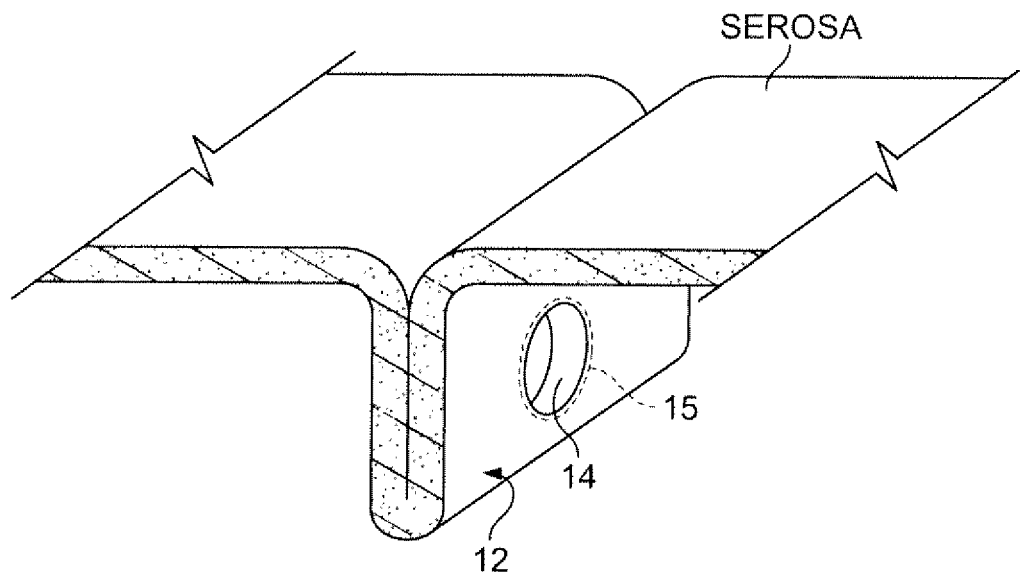
FIG. 2A is a partial section of a stomach wall showing a stomach wall plication having an opening formed in it.
Figure 2B:
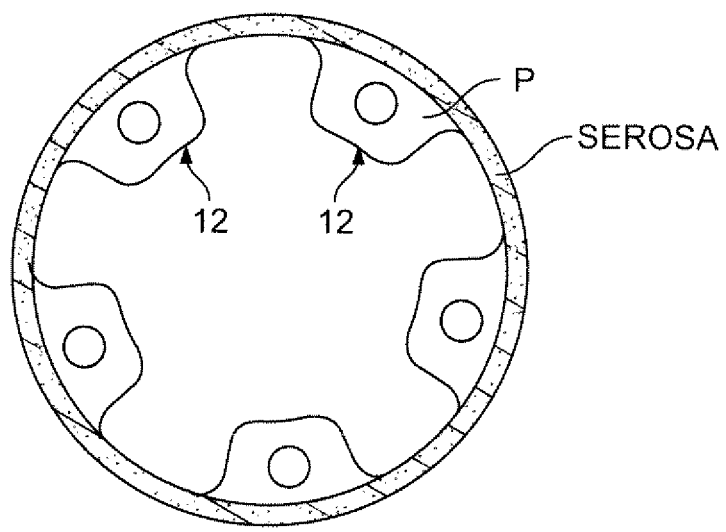
FIG. 2B is a cross-section view taken along the plane designated 2B-2B in FIG. 1, and illustrating five plications formed in a gastro-esophageal junction region of the stomach.

One type of tissue target that will be described herein, for illustrative purposes, is an anchor coupled to a tissue plication as illustrated in FIGS. 2A-2D. FIG. 2A shows a tissue plication 12 having an interior hole 14 formed therein and surrounded by one or more annular arrays of staples 15. In the exemplary embodiment described below for implanting a restrictive implant or pouch, referred to herein as a restrictor, five such plications are formed, as shown in FIG. 2B, approximately equally spaced about the esophageal/gastrointestinal junction in the stomach. Each plication will receive an anchor, such as anchor 16 shown in FIGS. 2C and 2D.

Figure 2C:
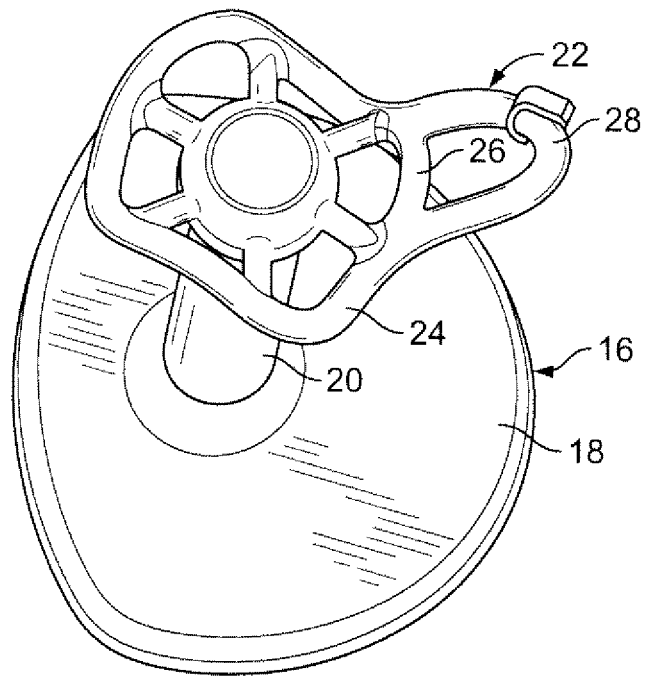
FIG. 2C is a perspective view of an anchor used in practicing an embodiment of the invention designed for attaching a food restrictive implant (restrictor) to the stomach.
Figure 2D:
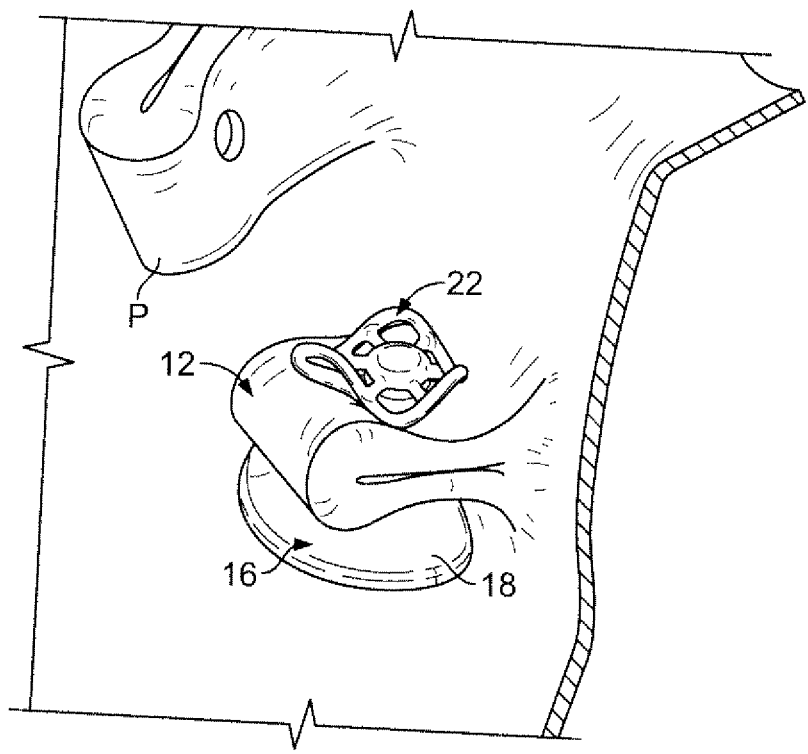
FIG. 2D is a perspective view of an anchor held in a tissue plication.

Representative anchor 16, which is shown in FIG. 2C, includes a base 18, a stem 20, and a head or cap 22. The anchor is formed using materials that are durable within the stomach environment, and provide desired elastomeric properties. For example, the cap may be molded out of a higher durometer compliant (elastomeric) material (such as 50 shore A durometer Silicone) while the stem and base may be molded out of a softer compliant material (such as 5 shore A durometer Silicone). Since the loading on the anchor from the restrictor implant can be seen as shear against the edges of the opening in the plication, the stem is formed to have a relatively large diameter (2 mm-8 mm) to minimize stress and abrasion on the stomach wall tissue inside the opening. The edges of the anchor are molded with a generous fillet radii to minimize abrasion of stomach wall tissue. Cap 22 includes a ring 24 and a plurality of struts 26 coupling the ring to the stem, as shown, and loop 28 extending from the ring.

The anchor is elastically deformable to an elongated shape in response to application of tension to the ring 24 or loop 28 (collectively referred to as the "rim"). This allows the anchor to be drawn into a streamlined shape so that it can be drawn through the hole in the plication, illustrated in FIG. 2D, and also through an aperture 38 in the restrictor, as shown in FIG. 2F. When the cap is pulled from the rim, its shape lengthens and slims down to fit through a much smaller hole. For example in one embodiment, in its natural state the cap has an outer head diameter of approximately 0.600 inch (15 mm), but in its streamlined orientation it can fit through a plication opening of 0.200 inch (5 mm). However, once implanted, the cap's shape resists pull-out force to a higher degree since the rim is not being pulled and lengthened directly. Also in this embodiment, the base is designed so it will not pull through the hole and may have an outer diameter of approximately 1 inch (25.4 mm).

Figure 2E:
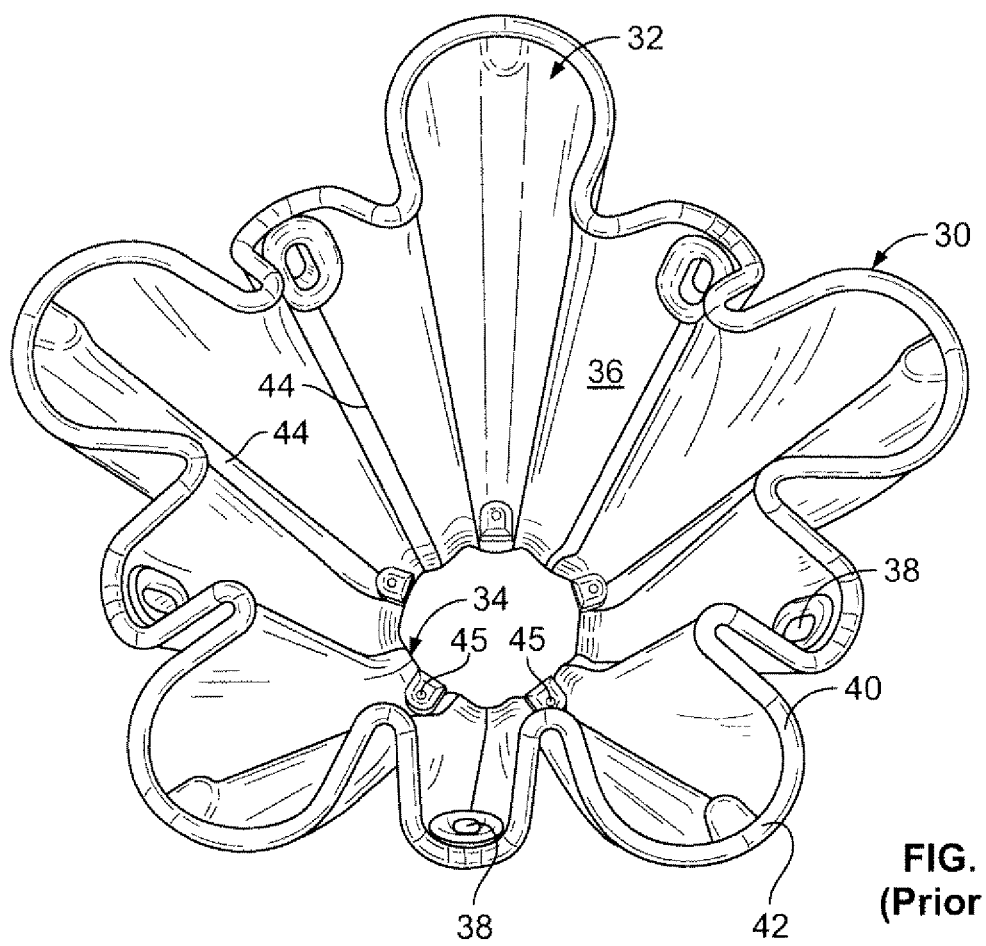
FIG. 2E is a perspective view of a restrictor employed in an embodiment of the invention.
Figure 2F:
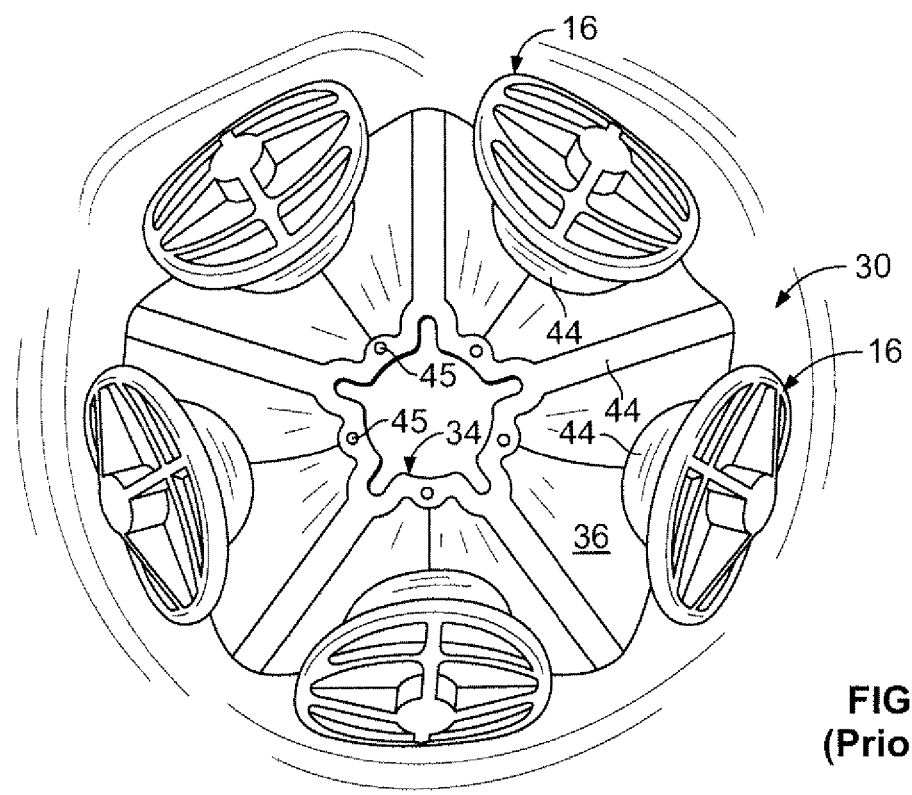
FIG. 2F is a perspective view of the restrictor attached within the stomach adjacent the gastro-esophageal junction.

The food-restrictive pouch or restrictor, shown at 30 in FIGS. 2E and 2F, is an implant designed to slow the passage of food from the esophagus into the stomach. The restrictor is positioned in the stomach such that food enters the restrictor through a proximal opening 32 and exits through a reduced-diameter distal opening 34. The restrictor and/or openings are proportioned to slow the rate at which food can move into or through the restrictor, and/or from the restrictor into the rest of the stomach.

In a preferred design, restrictor 30 includes features that minimize pulling against the anchors when the restrictor encounters stress as a result of food moving through the restrictor and/or movement of the stomach. Minimizing pulling at the anchors is beneficial for minimizing stress on the stomach wall tissue coupled to the anchors. In general, the restrictor 30 is designed to have compliance between the anchor points (i.e., the points at which the implant is coupled to the tissue directly or using the anchors). This compliance may be achieved using the geometry of the restrictor and/or using restrictor materials selected to give compliance between the anchor points.

In the embodiment shown in FIGS. 2E and 2F, restrictor 30 is a pouch having a wall 36 and a plurality of anchor apertures 38 formed in the wall and spaced about the proximal-end opening of the restrictor, each for receiving an anchor 16 therein in FIG. 2F, for coupling the restrictor to the anchors, and thus to the tissue plications formed in the stomach. The restrictor wall is may be undulating, as shown, defining multiple folds that give it compliance even when molded from a relatively more stiff material (such as 30 shore A silicone). When viewed from the side, the proximal edge 40 of the restrictor undulates to define peaks in the profile of the proximal edge, such as peaks 42.

As seen in FIG. 2E, the anchor apertures are positioned between the proximal-edge peaks. The apertures may be surrounded by reinforced sections formed using thicker regions of silicone, or a stronger material embedded in or attached to the silicone. Additional reinforcements, such as ribs 44, may extend from the proximal-end peaks towards the distal-end orifice 34.

The edge of the wall defining the distal-end orifice 34 preferably includes folds or undulations as shown, allowing the orifice to be compliant as well. In addition, small apertures 45 are arranged around the orifice to allow the restrictor to be coupled to the restrictor guide device of the illustrated invention, to deliver the restrictor into the stomach. Additional details of the tissue plication, anchor and restrictor are provided in co-owned PCT/US2008/008729.

Implant System and Device

Figure 3:
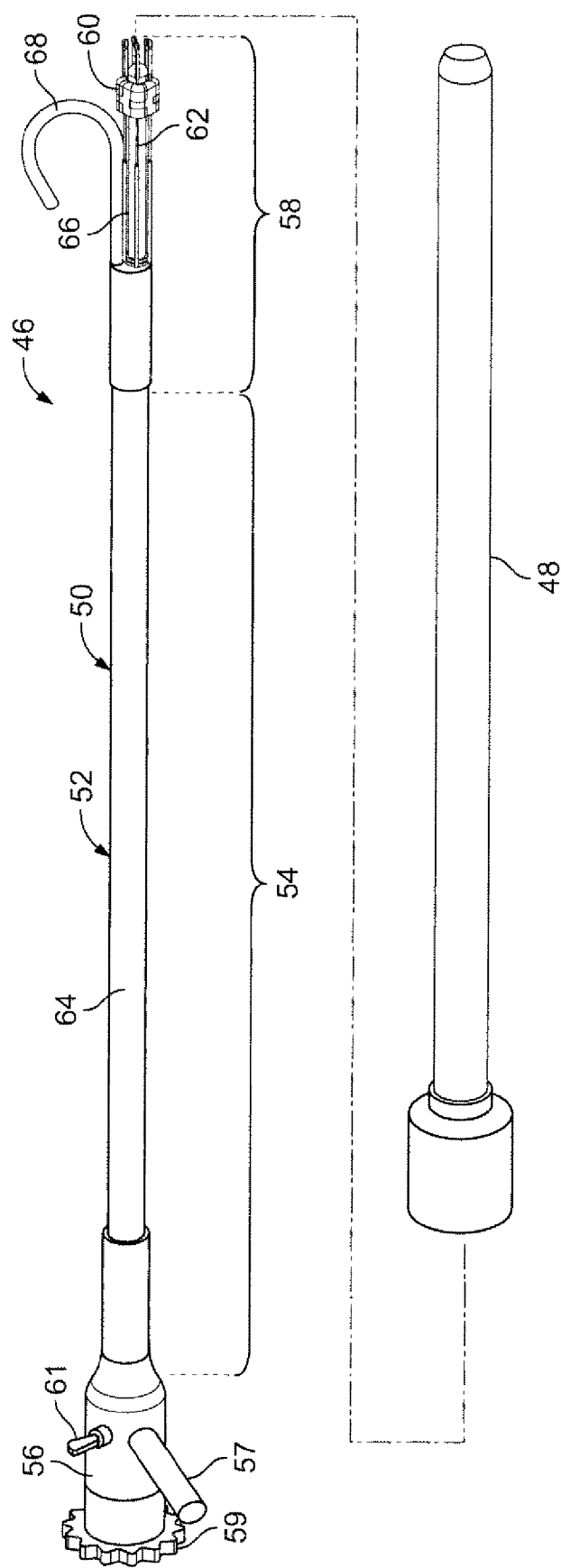
FIG. 3 illustrates an endoscopic implant system and device constructed in accordance with one embodiment of the invention.

FIG. 3 illustrates an endoscopic implant system 46 constructed in accordance with one embodiment of the invention, designed for implanting a restrictor of the type described above, by coupling the restrictor to a plurality of anchors supported in stomach plications, also as described above. However, it will be appreciated that the system of the invention may be used for a variety of purposes that involve (i) entry of the distal end of the system device into a hollow organ, and (ii) successively engaging and manipulating a plurality of spaced tissue targets within the organ.

System 46 includes an endogastric overtube 48 for establishing a working channel between the mouth and the stomach, and a device 50 designed to access a plurality of tissue targets in a hollow organ, e.g., stomach. Device 50 generally includes an elongate shaft assembly 52 having a proximal section 54 terminating at a proximal end 56 and a distal section 58 terminating at a distal end, and more particularly, a distal-end cable holder 60. Preferably, and as well be seen below particularly with respect to FIGS. 6A and 6B, the distal section is detachable from the proximal section, for replacement and/or cleaning.

Adjacent the proximal end of the shaft assembly are user controls, indicated at 57, 59, 61, for controlling steering and cable-member operations of the device, as will be described below. These operations are mediated by internal cables within the shaft assembly, according to well known construction, operation, and control of endoscopic tools and other remote-access surgical instruments, although hydraulic control of one or more of the device functions is also contemplated. Specifically, the controls are for (i) positioning the distal end of the shaft assembly, (ii) axial positioning of each of a plurality of cable members in the device (described below), and (iii) positioning of an endoscope in the device. In addition, where the cable members have actively controllable clamping tools (described below) additionally wire controls for these tools is provided.

Figure 4A:
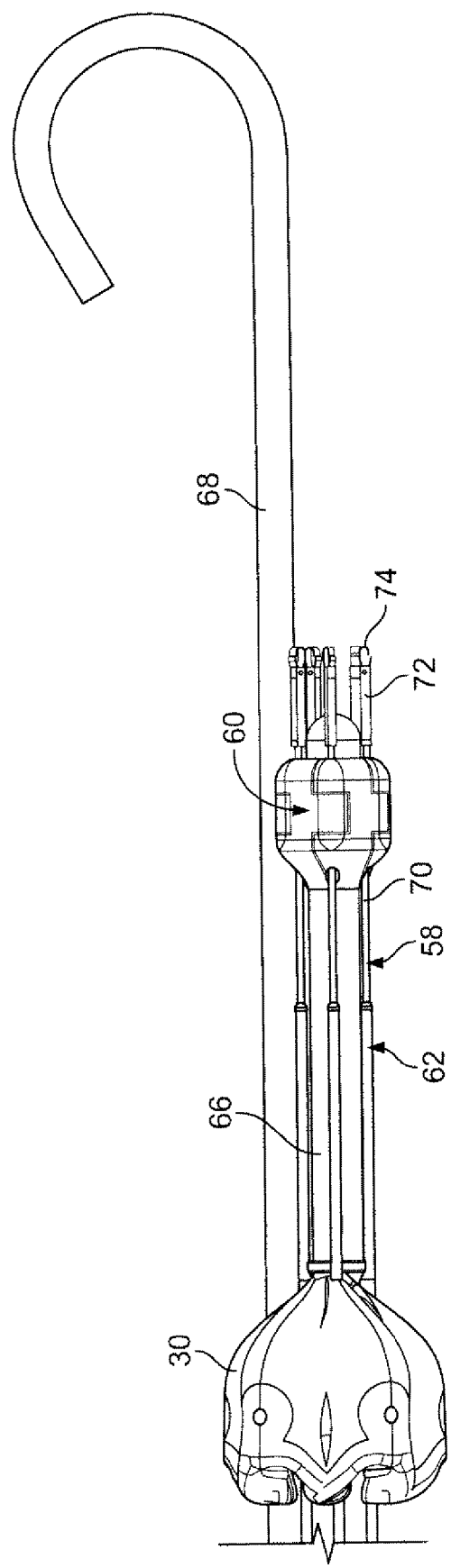
FIGS. 4A and 4B are side and perspective views, respectively, of the distal end region of the device shown in FIG. 3.
Figure 4B:
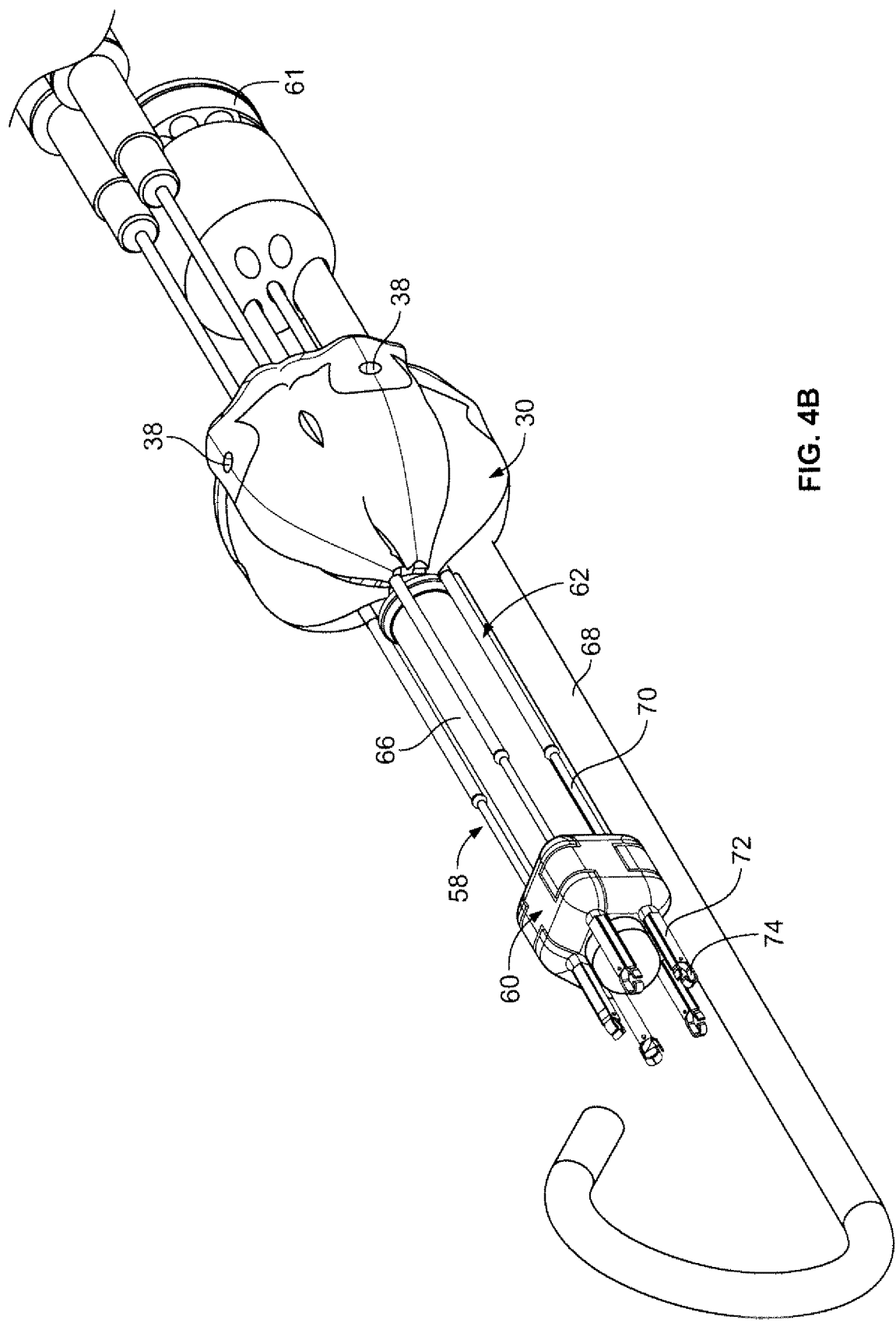

The shaft assembly includes an endoscope 58, a plurality of cable members, such as cable member 62 seen in FIGS. 4A, and 4B, and an internal steering guide (not shown), all of which are controllable from the proximal end in the assembly, as above, and all of which extend along the shaft assembly from the assembly's proximal to distal end regions. The endoscope conventionally includes an optical system, i.e., light source, lens and optical fibers, for visualizing the organ area near the distal end of the scope, and control cables within the endoscope for manipulating the position of the scope's distal end-region.

Along the shaft assembly's proximal section, the steering guide, cable members and endoscope are contained within an outer sheath or casing 64 (FIG. 3). Along the assembly's distal section, the steering guide is contained within and substantially coextends with a guide tube 66, to control the position of the holder 60 mounted on the end of the guide tube, by controlling the steering guide from the proximal end of the assembly. The steering guide and guide tube are also referred to herein as a steering mechanism for controlling the position of the assembly's distal-end holder.

Also as seen in FIG. 3 and FIGS. 4A and 4B, the endoscope and plural cable members 62 are exposed along the assembly's distal section, allowing the endoscope to be moved independently of guide tube 66 and holder 60, and allowing the guide tube and holder to be moved independently of the distal-regions of each cable member, after that cable member has engaged a tissue target, as will be described below. The proximal end of section 58, indicated at 61 in FIG. 4B, has a connector 61 for detachably coupling the distal section to the assembly's proximal shaft section. The connector is similar to a connector 84 described below with respect to FIG. 6B with respect to a second general embodiment of the device.

Cable member 62, which is representative, includes a cable 70 and a tool 72 carried at the distal end of the cable for engaging a tissue target. As indicated above, the axial position of the cable in each cable member, i.e., the cable's extended or retracted position along the shaft assembly, is controlled from a proximal-end control in the shaft assembly. Although not shown here, the portion of the cable assembly extending along the shaft assembly's proximal section (the portion within casing 64), is preferably housed in a cable sheath that provides a guide sleeve for axial movement of the cable. In the embodiment illustrated in FIGS. 3-5, the exposed portion of the cable member extending along the assembly's distal section is unsheathed.

Figure 5A:
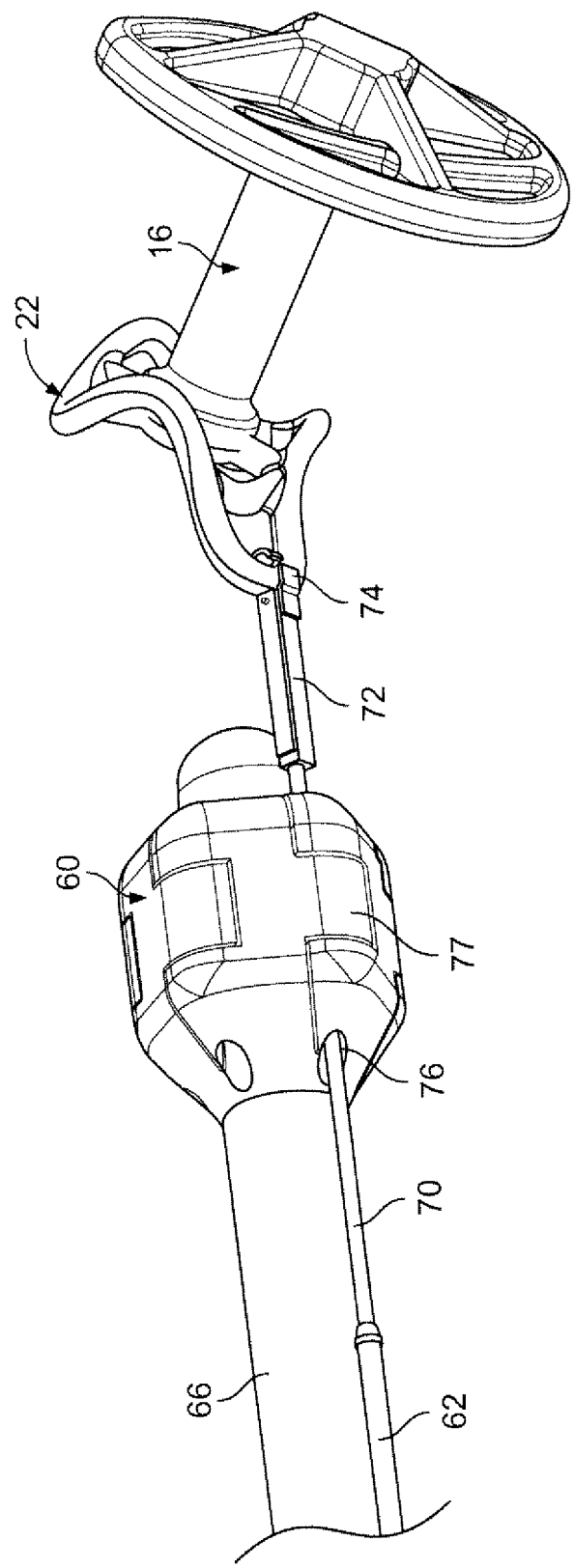
FIGS. 5A and 5B are perspective views of the distal end of the device illustrated in FIG. 3A, showing engagement of a cable-assembly tool with an anchor before (FIG. 5A) and after (FIG. 5B) release of the tool and engaged anchor from the holder at the end device.
Figure 5B:
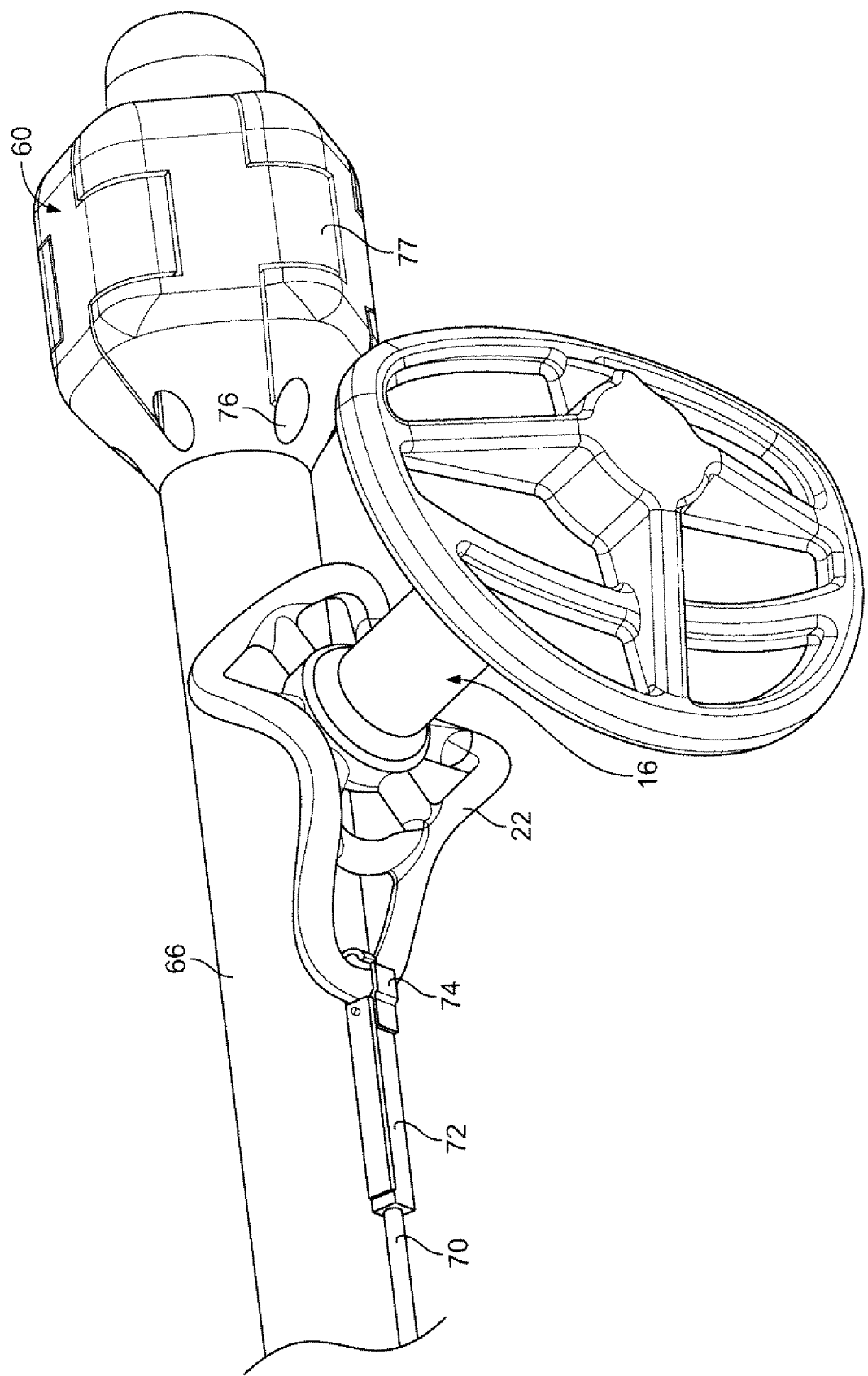

The cable member 62 shown in FIGS. 4 and 5 is representative and includes a cable 70 terminating in a distal-end tool 72 having a rigid open-ring hook 74 designed to engage the ring portion of an anchor cap as illustrated in FIGS. 5A and 5B. In this embodiment, the user manipulates the end of a cable assembly, as viewed through the endoscope to, to snare the anchor-cap ring 24 or loop 28 with hook 74. In an alternate embodiment (not shown), the tool includes a pair of clamping arms that are normally biased away from one another in a clamp-open condition, but can be retracted into a rigid sleeve at the end of the cable to draw the clamping arms moved to a closed, clamping condition. This embodiment includes a separate wire contained within the cable itself, for axial movement with respect thereto, to extend or retract the tool relative to the cable distal-end sleeve, to close and open the clamp, respectively. Such a tool is described, for example, in co-owned PCT/US2008/008729.

With reference FIGS. 4 and 5, holder 60 is a single-piece, preferably molded article formed of relatively firm, but flexible material, such as a relatively rigid silicone. The holder includes a plurality of axially extending slots, one for each cable assembly, such as slot 76 for cable member 62 (FIGS. 5A and 5B), and is dimensioned to allow axial movement of the cable within the slot, allowing the end of cable member to be pulled substantially against the holder, when it is desired to move the cable member with the holder, and to play out the cable member, to provide slack in the cable member to allow the holder to be moved independently with respect to the holder, after the cable member has engaged a target tissue. Each holder slot is covered by a deformable flap 77 which, in its undeformed condition (shown in the figures) covers the slot and supports the cable assembly within the slot, as seen in FIG. 5A, which shows a cable tool and attached anchor (the tissue target) being retracted toward holder 60. With continued cable retraction, the tool and attached anchor are blocked from entry into slot 76, causing flap 77 to deform sufficiently to allow the tool and attached anchored to be pulled out of the slot, thus releasing cable assembly from the holder.

In the embodiment just described, the release structure in the holder that serves to releasably attach each cable member in the holder is a deformable flap that provides a passive release mechanism for cable release when the cable and an attached tissue target are pulled against the holder. It will be appreciated that a variety of other passive release structures for releasably supporting a cable member in the holder are suitable. For example, the deformable flap may be replaced by a spring mechanism that holds the cable member in its captured condition until a sufficient counterforce to the spring is applied. Alternatively, the release structures may include open channels or grooves formed along the holder and dimensioned to hold a rigid sleeve at the end of each cable member, such that retracting a cable member with an engaged anchor first pulls the anchor against the sleeve, then pulls the sleeve out of the holder groove. In still another embodiment, described below with respect to FIGS. 6-8, the release structure is provided by a distal-end fixture on the cable assembly that provides both an axial channel for cable movement, and an element designed to interlock by friction fit with a complementary element on the holder, to attach the cable assembly to the holder.

The invention also contemplates actively controlled release structures, such as a spring-tensioned release mechanism or a solenoid device whose operation between closed, capture and open, release conditions can be controlled by a user at the proximal-end controls. However, a passive release structure, such as detailed above, provides advantages in simplicity of construction and operation.

Completing the description of the assembly, and with reference to FIG. 4B, distal section 58 includes a restrictor mount for carrying a restrictor 30 on the assembly in an implantation operation. The mount is not visible in the figure, but is similar to the restrictor mount described below with reference to FIGS. 7B and 7C. In the fully assembled device (see below), the cable members, such as members 62, are each received through a corresponding restrictor aperture, such as apertures 38 shown in FIG. 4B, so that the cable members, when placed under moderate tension, serve to press and deform the restrictor against the assembly, preventing release of the restrictor from the assembly until the final cable member has been released.

Second General Embodiment

Figure 6A:
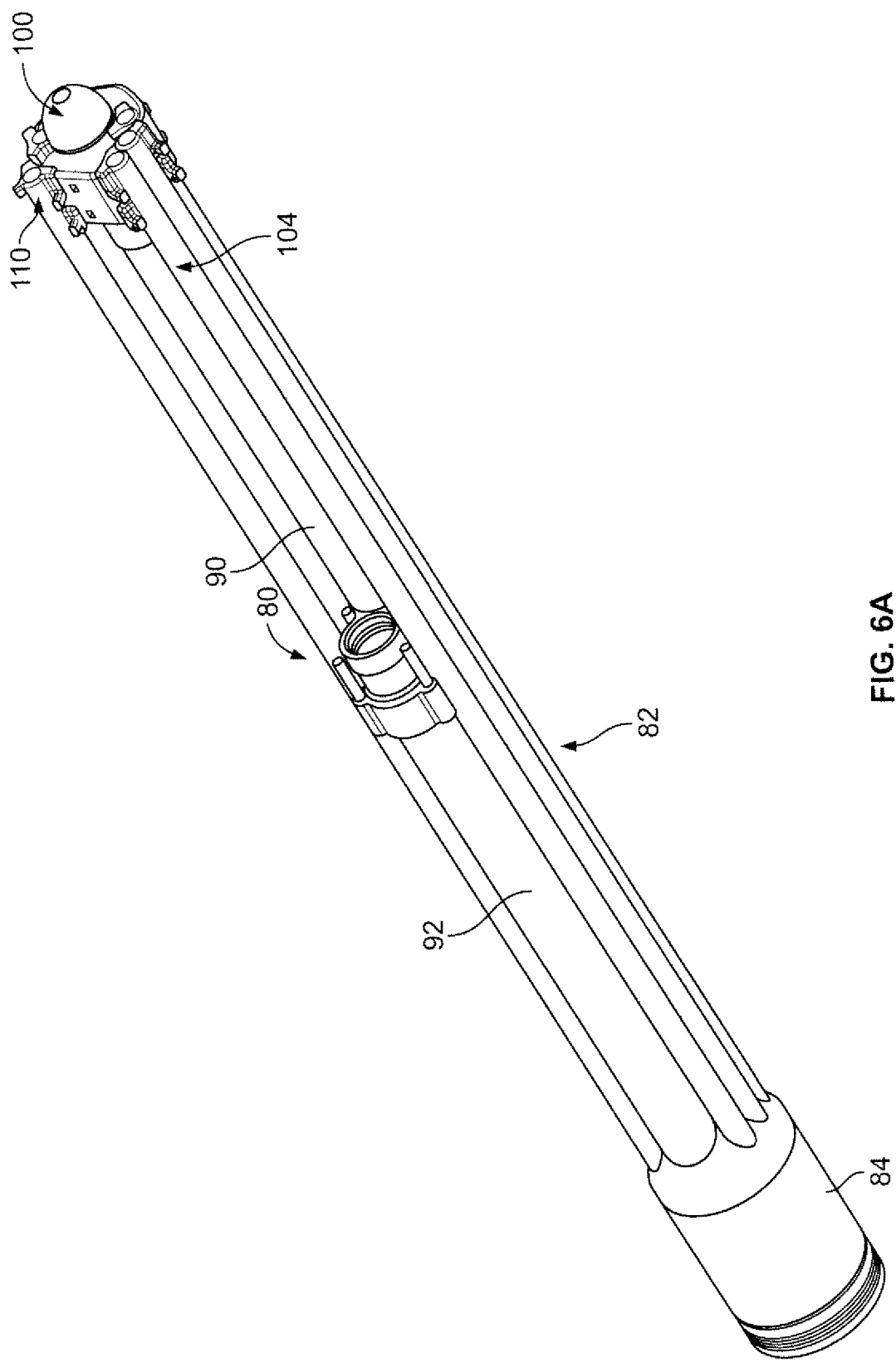
FIGS. 6A and 6B are perspective views of the distal end section of a device constructed according to an alternative embodiment of the invention.
Figure 6B:
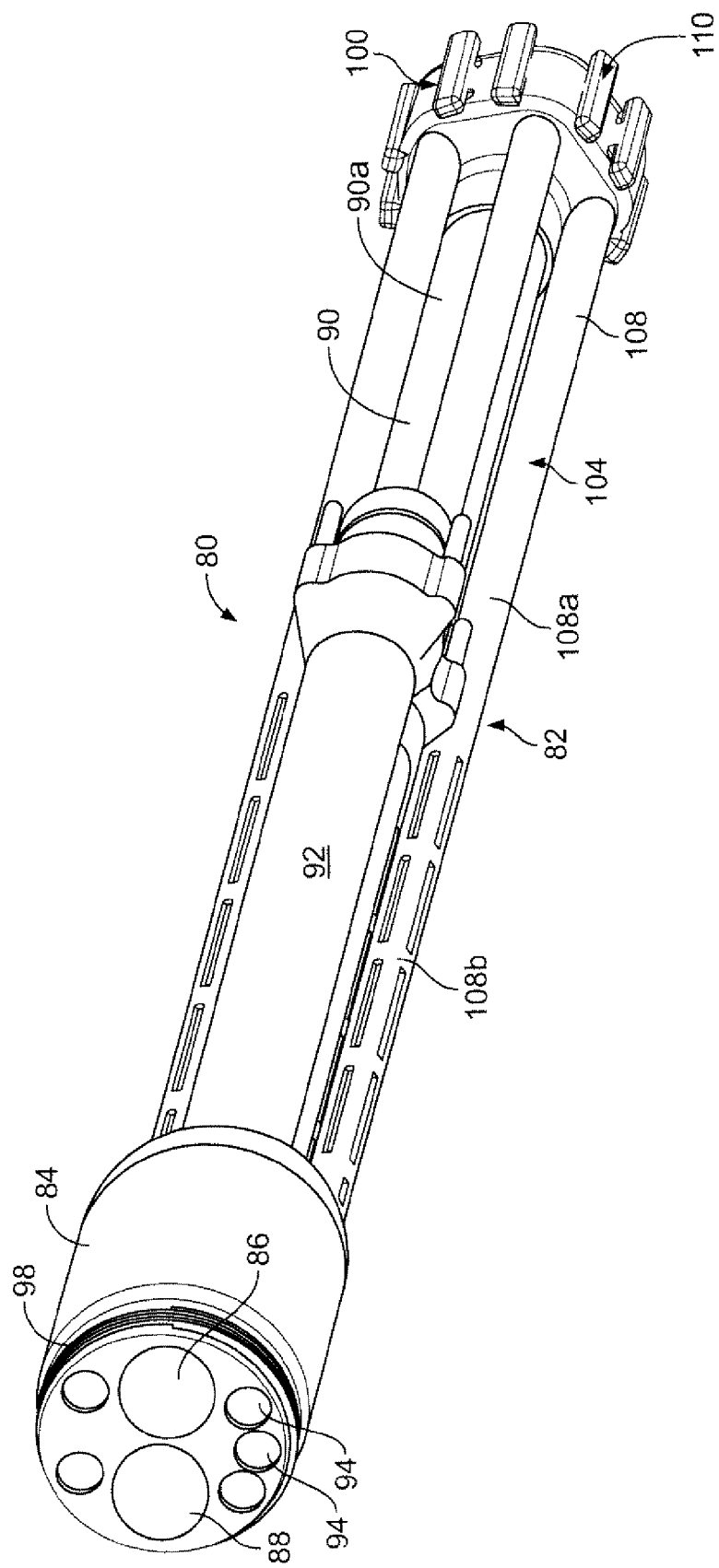
Figure 7C:
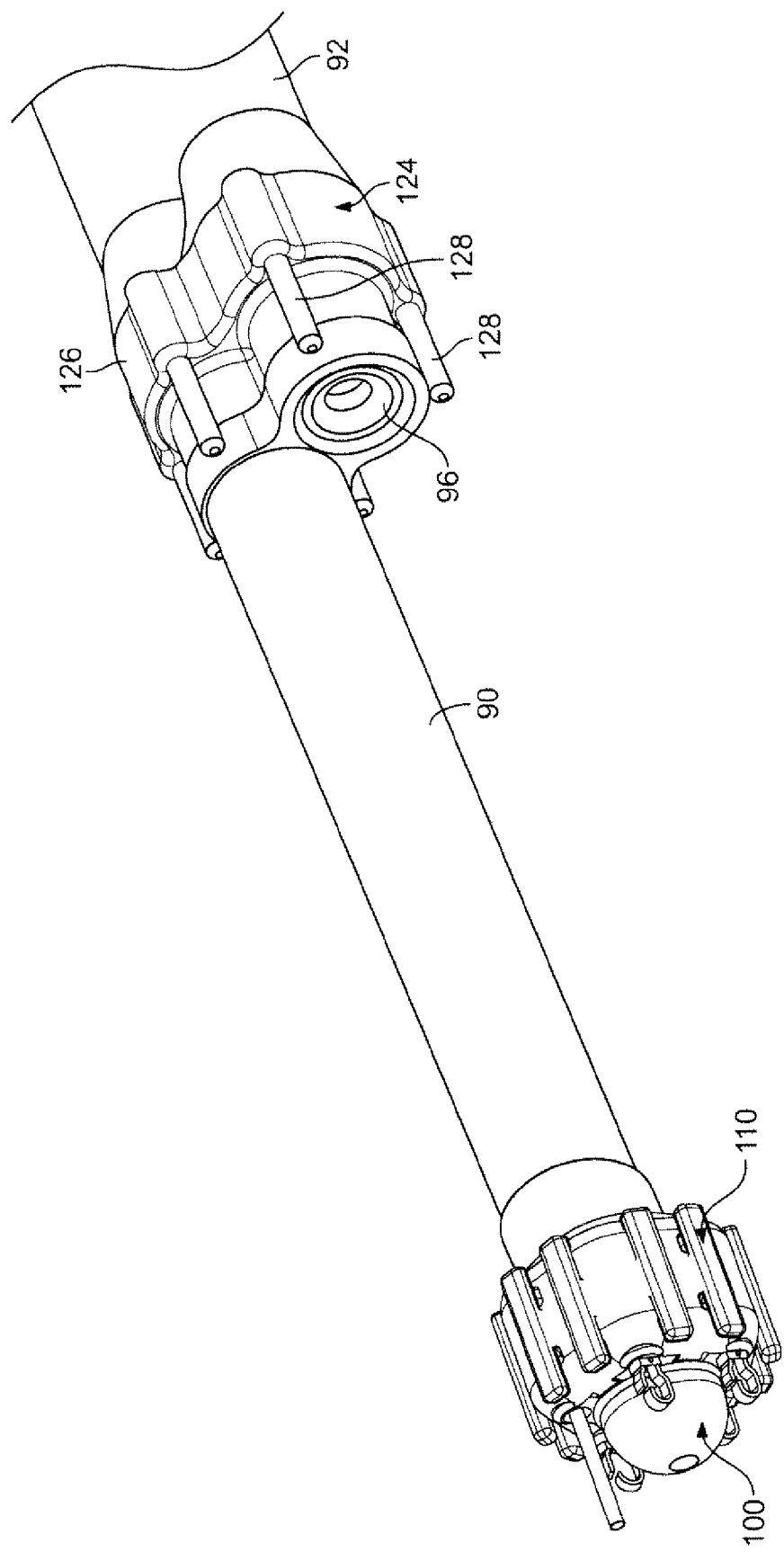

FIGS. 6-8 illustrate distal-end portions of an implantation device constructed in accordance with a second general embodiment of the invention. It will understood that the system and device of this second embodiment include the same or similar components as the first-described embodiment, except with respect to the distal-section elements illustrated in FIGS. 6-8. It will be further understood that certain features of this second embodiment may be incorporated into the first embodiment, particularly the detachable connection between the proximal and distal shaft sections, described with respect to FIG. 6B, and the restrictor mount for supporting a restrictor on the distal section of the shaft assembly, described with respect to FIGS. 7B and 7C.

FIGS. 6A and 6B are perspective views of a detachable distal section 80 in a shaft assembly 82 in the device of the invention. The section includes a proximal end connector 84 by which the distal section is removable attached to the proximal end section (not shown) of the shaft assembly. As seen in FIG. 6B, connector 84 has a pair of openings 88, 86, which correspond to the lower (proximal) ends of a guide tube 90 and an endoscope tube 92, respectively, and five channels 94 through which the five cable members in the device are received. To attach the distal section to the proximal section, the portion of an endoscope (not shown) extending beyond the end of the assembly's proximal section is inserted into opening 86 and through tube 92, exiting through opening 96 shown in FIGS. 7B and 7C; the portion of the steering guide extending beyond the end of the shaft assembly's proximal section is inserted through opening 88 into and though substantially the entire length of guide tube 90; and the portions of the five cable members (see below) extending beyond the end of the shaft assembly's proximal section are inserted through channels 94. The distal section is then secured to the proximal section by a threaded ring rotatably attached to the end of the proximal section, and engageble with threads 98 at the lower end of connector 84. As described with respect to the first embodiment, the steering guide contained with guide tube 90 is used for controlling the position of the guide tube from the shaft assembly's proximal end. The steerable guide and guide tube are also referred to herein as a steering mechanism for controlling the position of the assembly's distal-end holder.

The steerable distal portion of the guide tube, indicated at 90a in FIG. 6A, terminates in a distal-end holder 100. As in the embodiment described in FIGS. 4 and 5, the holder is designed for releasable attaching a plurality of cable members, such as cable member, 104, through associated release structures, but in this embodiment, the release structures are distal-end fixtures 110 (described below with respect to FIG. 7A) that are attached to the holder by friction-fit elements, and which are released from the holder with the cable assembly.

A plurality of cable members in the device, such as cable member 104 in the figures, are operable to engage a tissue target within the organ and to manipulate the engaged target in accordance with the desired operation of the device, for example, to engage a tissue-plication anchor and pull it through an anchor aperture opening in a restrictor carried on the device. Cable member 104, which is representative, includes a cable 106 (FIG. 8A) that extends the length of shaft assembly and which can be manipulated at the proximal end of the shaft assembly, as above. Proximal and distal portions of the cable, corresponding roughly to the shaft assembly's proximal and distal shaft assembly regions, respectively, are housed within proximal and distal cable sheaths, respectively. The proximal and distal sheaths may be formed as a single uniform sheath. More preferably, however, the proximal sheath is a relatively stiff, relatively incompressible sheath, and the distal sheath is a relatively thin-wall compressible sheath, as discussed below. As in the first embodiment, the steering guide, cable members, and endoscope are housed within a outer casing along the shaft assembly proximal section, but are exposed for independent movement along the shaft's distal portion, that is, beyond connector 84.

FIGS. 6A and 6B show the distal sheath 108 of a cable member 104. A s noted above, the portion of each cable member that is co-extensive with distal section 80 is secured at its proximal end within connector 84, and releasably attached at its distal end to holder 100. So mounted on the shaft assembly's distal section, and with the cable member's distal end pulled against holder, the distal end of the cable member is constrained to move with the holder as the guide tube is manipulated to a selected position within an organ. However, by virtue of playing out additional cable in the cable member or by virtue of the cable member detaching from the holder, the holder and its remaining attached cable members may be repositioned within an organ, substantially independently of the cable member that is engaged with a tissue target. As will be seen below, this feature allows all of the cable members to be guided successively, under the control of a single guide structure, i.e., guide tube 90, but allows the holder to be moved independently of each cable member, after that cable member has engaged a tissue section and been released from the distal-end head.

In the embodiment shown, for use in attaching tissue plication anchors to a restrictor, the end of each cable member (and the engaged tissue-target anchor) must be pulled in a proximal direction, by retracting the cable, to engage the restrictor, which is carried on the shaft assembly near the end of the endoscope tube 92, as seen in FIG. 7B. This distal cable movement is accommodated by compressing sheath 108 axially, in essence, forcing it to bunch up as its length is reduced. To this end, the sheath is preferably formed of a thin-walled plastic tube material. Further, all or a portion of the sheath may be slotted to further accommodate axial shortening of the sheath. In the embodiment shown in FIG. 6B, sheath 108 has a slotted portion 108b and an unslotted distal portion 108a. As the tool and attached anchor are retracted, the anchor cap will be pulled through an aperture 38 in the restrictor, thus coupling that anchor to the restrictor. The cable members may be color coded or otherwise identified to assist the user in matching a selected cable member with a selected tissue-plication during an implantation operation, as described below.

Figure 8A:
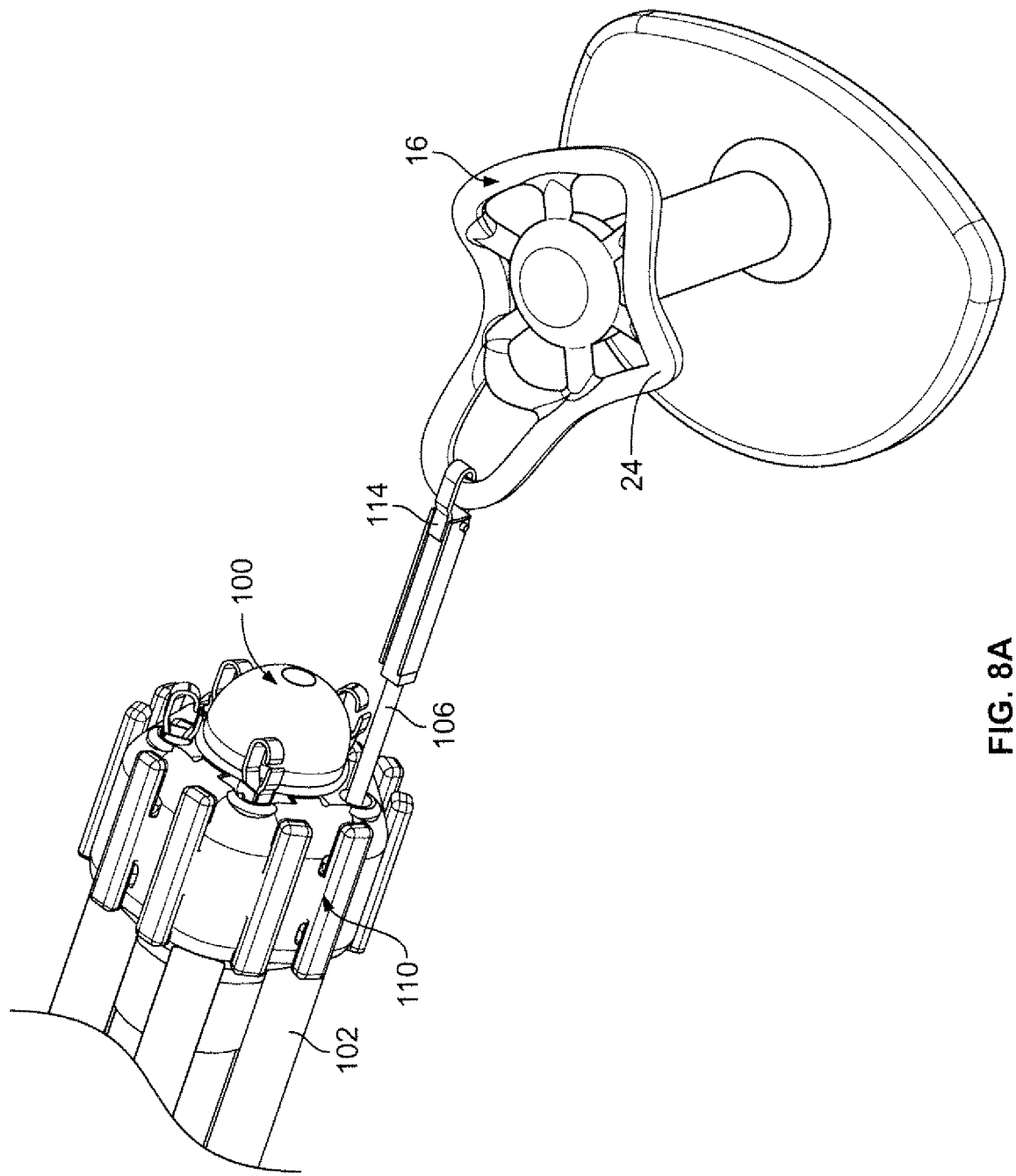
FIGS. 8A and 8B are perspective views of the distal end of the device illustrated in FIGS. 6A and 6B, showing engagement of a cable-assembly tool with an anchor before (FIG. 8A) and after (8B) release of the tool and engaged anchor from the holder at the end device.

With reference particularly to FIG. 7A, distal sheath 108 in cable member 104 terminates at a distal-end fixture 110 that provides structure for releasably attaching the cable member to holder 100, and also provides a rigid sleeve 112 at the end of the sheath for engaging a tool 114 attached to the end of the cable (FIG. 8A). Fixture 110, which may be formed as a molded, rigid plastic article, has a curved body 116 whose lower surface is shaped to fit against the cylindrical end of holder 100, seen best in FIG. 8B, and a central bore 118 which forms a slot or channel through which the cable is axially shiftable. Fixture 110 is provided by a pair of wings 120 extending from opposite sides of the body. These wings each have, on their lower surfaces in FIG. 8A, a pair of projections 122 which are dimensioned to be received snugly within corresponding openings 124 in holder 100 (FIG. 8B), to releasably attach the end of the cable member to holder 100. That is, the projections and openings provide complementary friction-fit elements for releasably attaching the cable member to the holder.

Figure 8B:
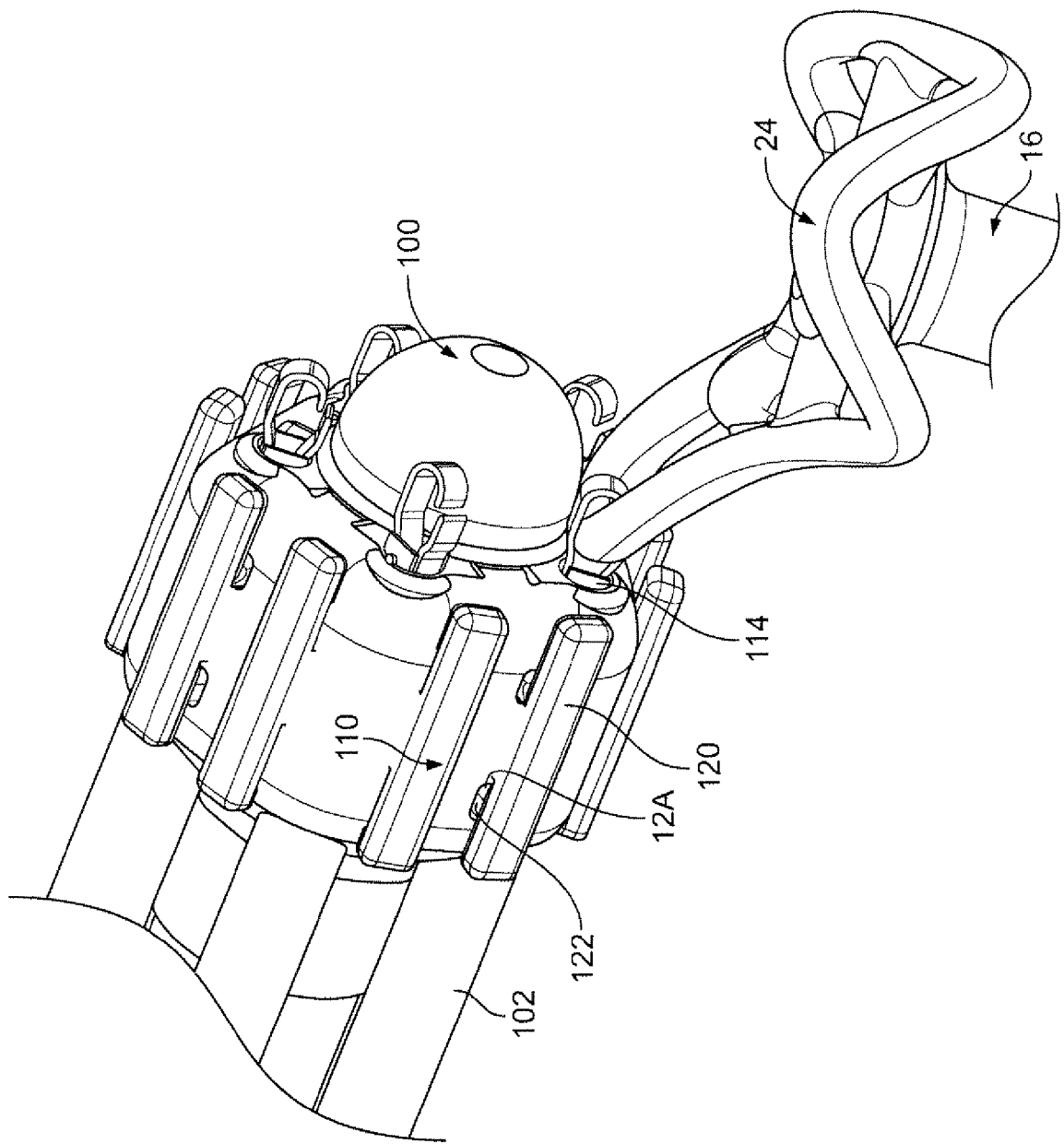

Referring particularly to FIGS. 8A and 8B, tool 114 carried at the end of cable 106b is designed to for engaging a selected tissue site when the cable is position adjacent the target. In the embodiment shown, tool 114 is a open-ring clamp of the type described above, allowing the clip to engage a tissue target, such as ring 24, in an anchor 16 (FIG. 8A). In a related embodiment, the two arms of the tool may be spring biased away from one another, allowing the clip to open when its base portion is advanced out of the sleeve in the fixture and to close for clamping when the cable is retracted to pull the tool arms partially into the fixture.

As seen in FIG. 8B, tool 114 is outwardly flared at its proximal (lower) end, providing contact structure for blocking entry of the clip into the corresponding fixture sleeve. More generally, one of the engaging tool and sleeve member provides contacting structure for restricting movement of the tool into the sleeve member.

In another embodiment (not shown), the distal-end fixture in the cable member may be a cylindrical sleeve which is received, e.g., by friction fit, in a corresponding open channel formed in the holder, where retraction of the tool and engaged tissue target against the fixture blocks further movement of the cable member with respect to the fixture, such that further retraction of the cable member causes the fixture to be pulled from the holder channel, releasing the cable assembly fixture from the holder.

Also included in the distal section is a restrictor mount for supporting a restrictor 30 on the distal section, as seen in FIGS. 7B and 7C. As seen in these figures, endoscope tube 92 terminates in a manifold 124 which has an enlarged circumference base 126 which supports a plurality of posts 128 used in mounting a restrictor 30 on the distal shaft assembly section, as seen in FIG. 7B. In the embodiment shown, the device include five posts for engaging the five apertures 45 in restrictor 30, as shown in FIG. 7A. The manifold and posts are also referred to herein as a restrictor mount for supporting a restrictor on the assembly during an implantation operation.

An endoscope in the device, like the one shown and described at 68 in FIG. 3 for the first-described embodiment, extends along the shaft assembly from the proximal end thereof, where the user controls endoscope position, through connector 84 and through an opening 96 in manifold 124 beyond which the endoscope is freely movable, for viewing operations of the device within the hollow organ.

Preparing the Device for an Implant Operation

The preparation of the device for implanting a restrictor to tissue-plication anchors in a patient's stomach will be described with respect to the embodiment of FIGS. 6-8, it being understood that similar loading and preparation steps apply to the embodiment described with respect to FIGS. 4 and 5. Initially, the two shaft sections are coupled together by feeding the endoscope tube, steering guide and five cable members through connector 84 and securing the two sections together. Color coding or other distinctive indicia on each cable member allow the user to determine the identity of each cable member and its relative position on the shaft assembly at the proximal end of the tool during an implantation operation, A restrictor is then placed on the shaft assembly's distal section, as shown in FIG. 7B, with the posts 128 on the manifold base 124 received in apertures 45 in the restrictor.

The cable assemblies are next threaded through apertures 38 in the restrictor, and the ends of the cable assembly are releasably attached to the holder, e.g., by securing the distal-end fixtures in the cable assembly to the holder, or, in the first embodiment, by threading the ends of the cable assembly through the holder slots.

It can be appreciated from FIGS. 6A and 6B that attaching the distal ends of the cable members to the distal-end holder 100 acts to stretch the cable members along the distal shaft assembly region, deforming the restrictor against the distal shaft assembly section, to secure restrictor in a compact condition during placement of the restrictor in the stomach by passage through overtube 48. In the final preparation step, an overtube is placed over the assembled shaft, the overtube's distal end being positioned to cover the restrictor carried near the shaft's distal end.

Implant Operation

The initial phase of a restrictor implant operation involves forming tissue plications at plural selected locations, as shown in FIG. 2B, and attaching anchors within each plication hole, as described for example, in co-owned U.S. application Ser. No. 12/175,242, filed Jul. 17, 2008, corresponding to PCT application PCT/US2008/008729. This phase of the operation may be carried out several days to weeks in advance of implanting the restrictor, to allow healing of the plications, or may be carried out immediately before implantation, as part of an operation in which the same overtube is used for accessing the stomach for forming tissue plications with attached anchors and for restrictor implantation.

With the implantation device prepared as described in the section above, the overtube and device are inserted in the patient for transoral access to the stomach, the present device is inserted into the stomach to place the distal-end holder 100 in the region of the tissue plications near the gastro/esophageal junction. Using the endoscope for guidance, the physician will select a given plication, and maneuver the distal section of the shaft assembly, by controlling the steering guide in the device, to place a selected cable member tool, e.g., identified by its color code, adjacent the anchor at that plication. That cable member is now manipulated, by extending the cable in a distal direction, to engage the target anchor with the tool, by moving the tool, if necessary, until the tool clip hooks onto the anchor cap ring.

Once engagement with a tissue-plication anchor is made, the device is manipulated to place a next-in-place cable assembly tool adjacent a next-in-place tissue-plication anchor. Movement of the holder from the first to the second anchor is accommodated by either playing out cable in the engaged cable assembly, to provide cable slack between that assembly and the holder, or by retracting the engaged cable assembly until it is released from the holder, it being understood that ultimately, each engaged cable must be released from the holder to pull the engaged anchor through the associated aperture in restrictor 30. That is, the cable members may be operated to successively engage multiple anchors before any member is released from the holder, or the cable members can be operated to successively engage an anchor, be released from the holder, and couple to the restrictor before the next-in-line cable assembly is engaged with the next-in-line tissue-plication anchor.

In either event, once a cable member is retracted, the cable member tool and engaged anchor are initially pulled against the associated release structure, then released from the holder, by the release structure releasing the cable member from the holder. Continued retraction of the cable assembly pulls the engaged anchor toward the restrictor, and continued retraction, with endoscopic observation, pulls the anchor cap through the corresponding anchor aperture 38 in the restrictor. The cable member may be further manipulated, to release the tool from the now-coupled anchor, or the tool may be retained in its engaged condition until all of the anchors have been coupled to the restrictor.

The process is repeated until all, e.g., five, plication anchors have been coupled to the corresponding restrictor aperture. If the cable members are still engaged with the anchors at this point, they are individually manipulated to release them from the anchors, The restrictor is now fully coupled to the tissue plications, so that with careful retraction of the implantation device, the restrictor will slide off the device and assume a fully expanded condition within the stomach.

From the foregoing, it will be appreciated how various objects and features of the invention are met. First, the multiple cable members in the device, each one required for engaging a separate tissue section and for manipulating the engaged section with respect to an implant, are maneuvered into desired positions within a hollow organ by a single steering mechanism, rather than requiring an independent steering mechanism for each cable member. This significantly reduces the amount of space, i.e., overall shaft assembly diameter required, allowing construction of a multiple assembly tool that can operate within the constraints of a transoral overtube. As noted above, movement of the distal-end holder to another tissue target, after engagement with a first target, is accommodated by playing out cable in the engaged cable member to create cable slack between the holder and engaged cable member, and/or by releasing the cable member from the holder.

The cable-assembly release feature allows the released cable assembled to be manipulated, e.g., retracted for coupling to the implant, independently of the shaft assembly's distal section and the remaining attached cable members. By the same token, the shaft assembly and still-attached cable members can be maneuvered to another selected tissue target, substantially independent of the released cable members. In one preferred embodiment, the cable release is effected by passive release, simply by retracting the cable with enough force to pull it away from its distal-end holder.

In the second general embodiment described above, the compressible cable sheaths in the device allow for normal cable operation, that is, movement of a cable within a guiding cable sleeve or cover, while still permitting the assembly to be retracted significantly to couple an engaged anchor with an implant carried on the shaft assembly of the device, as described above.

Finally, the device in one preferred embodiment allows the distal section of the device to be easily removed for cleaning and/or replacement. Although the attachment between the two shaft assembly sections was illustrated herein as a rotating ring attachment, it will be appreciated that the construction of the device is easily adaptable to a quick-lock type attachment.

Although the invention has been described with respect to particular embodiments and applications, it will be appreciated how the invention can be modified without departing from the spirit of the claims.

It is claimed:

1. An endoscopic device for engaging a plurality of spaced tissue targets within a body of a subject, comprising:
   an elongate shaft assembly extending from a proximal end to a distal end;
   a plurality of cable members extending from the proximal end to the distal end of the shaft assembly, wherein each cable member of the plurality of cable member includes a distal-end tool adapted to engage a selected tissue target within the body;
   a cable holder at the distal end of the shaft assembly, wherein the cable holder includes a release structure by which that each cable member of the plurality of cable members is detachably attached to the cable holder, wherein detaching a first cable member of the plurality of cable members from the cable holder disconnects the first cable member from the cable holder and allows the cable holder with the remaining attached cable members to be repositioned within the body.

2. The device of claim 1, which further includes an endoscope extending along the shaft assembly and being independently movable with respect to the cable holder at the distal end of the shaft assembly.

3. The device of claim 1, wherein a proximal portion of each cable member is disposed within a shaft assembly casing extending along the proximal section of the shaft assembly, and an exposed distal portion is disposed outside the shaft assembly along the distal section thereof, which is substantially less than proximal portion.

4. The device of claim 3, wherein the portion of each cable member disposed within the shaft assembly casing is housed within a cable sheath.

5. The device of claim 4, wherein the exposed portion of each cable member disposed outside the shaft assembly casing is housed within a longitudinally compressible sheath allows that distal end of the cable to be retracted, shortening the length of the exposed portion of the cable member.

6. The device of claim 5, wherein the distal sheath of each cable member has longitudinally extending slots, to enhance the axial compressibility of the sheath.

7. The device of claim 5, wherein the release structure for each cable member includes a distal-end fitting that is carried at the distal end of the cable-member sheath and that is releasably attached to the holder by friction fit, and the distal-end fixture is dimensioned to block the cable tool and attached tissue target, such that retracting the cable and engaged target against the fixture is effective, with further retraction, to release the cable member and engaged tissue from the holder.

8. The device of claim 1, wherein the holder includes, for each cable member, an elongate slot and the release structure includes a passive capture member adapted to releasably hold the cable assembly within the slot, for movement therein, but deform when the tool and an engaged tissue target are pulled away from the slot, to release the cable member and engaged tool from the holder.

9. The device of claim 1, wherein the holder includes, for each cable member, an elongate slot and the release structure includes an active capture member whose operation can be controlled between a capture position, in which the cable assembly is supported within the slot, for movement therein, and a release position in which the cable member and engaged tissue target are released from the holder.

10. The device of claim 1, wherein each cable member includes an inner wire that is shiftable within the cable member, and the distal-end tool includes a pair of clamp arms carried at the distal end of the wire, such that movement of the wire within the cable member in distal and proximal directions is effective to open and close the clamp arms, respectively.

11. The device of claim 1, for use in attaching a restrictor within a subject's stomach to a plurality of tissue targets having anchors fastened to tissue plications within the stomach, where the restrictor includes a proximal opening and a plurality of apertures spaced about the proximal opening, each for engaging an anchor to attach the restrictor within the stomach, wherein the shaft assembly includes a distal-section restrictor mount for holding the restrictor releasably on the shaft assembly, with the cable members received through said apertures, and said cable-member tools are adapted to clamp the anchors, such that withdrawing a cable of a selected cable member, after clamping a selected anchor, is effective to release the cable member from its release structure in the distal-end holder, allowing the tool and engaged anchor to be retracted distally until a cap portion of the anchor is pulled through the associated aperture in the restrictor.

12. The device of claim 11, wherein the restrictor has a central distal opening, is adapted to be carried on the device with a distal portion of the shaft assembly inserted through the distal opening in the restrictor, and is forced into a collapsed condition when the cable members are attached to the distal-end holder.

13. The device of claim 12, which further includes a restrictor mount having a plurality of posts disposed about the shaft assembly at a position along the shaft assembly's distal end section, for mounting the restrictor on the shaft assembly, with the posts received in apertures spaced about the restrictor's distal opening, and wherein the restrictor can be disengaged from the device only when all of the cable members have been released from the holder.

14. The device of claim 1, wherein the elongate shaft includes a proximal section removably coupled to a distal section.

15. The device of claim 1, wherein a separate distal-end tool is coupled to each cable member of the plurality of cable members.

16. A system for implanting in a restrictor device in a patient's stomach, the restrictor device including a plurality of spaced apart apertures comprising:
   (A) an implantation device comprising an elongate shaft assembly extending from a proximal end to a distal end, the shaft assembly including:
      a plurality of cable members extending from the proximal end to the distal end of the shaft assembly, wherein each cable member of the plurality of cable member includes a distal-end tool adapted to engage a selected tissue target within the stomach;
      a cable holder at the distal end of the shaft assembly, wherein the cable holder includes a release structure by which each cable member of the plurality of cable members is detachably attached to the cable holder, wherein detaching a first cable member of the plurality of cable members from the cable holder disconnects the first cable member from the cable holder and allows the cable holder with the remaining attached cable members to be repositioned within the stomach;

a restrictor mount configured to support the restrictor device thereon with each cable member of the plurality of cable members passing through a separate aperture of the plurality of apertures of the resistor device; and (B) an overtube configured to direct the implantation device into the patient's stomach transorally.

17. The system of claim 16, wherein the restrictor mount in the device has a plurality of posts positioned about the shaft assembly, with the posts received in apertures spaced about the restrictor's distal opening, and wherein the restrictor can be disengaged from the device only when all of the cable members have been released from the holder.

18. The system of claim 16, wherein the overtube is movable on the device shaft assembly between extended and retracted positions at which the overtube covers and exposes the restrictor mount and restrictor carried thereon, respectively.

19. The system of claim 16, wherein the elongate shaft of the implantation device includes a proximal section removably coupled to a distal section.

20. The system of claim 16, wherein the restrictor device is a device configured to restrict flow of food into the stomach, the restrictor device including a central opening configured to direct food from an esophagus into the stomach, the plurality of spaced apart apertures being positioned about the central opening.

* * * * *